United States Patent
Allerson et al.

(10) Patent No.: US 12,005,120 B2
(45) Date of Patent: Jun. 11, 2024

(54) GALNAC CONJUGATED MODIFIED OLIGONUCLEOTIDES AS miR-122 INHIBITOR HAVING HCV ANTIVIRAL ACTIVITY WITH REDUCED HYPERBILIRUBINEMIA SIDE-EFFECT

(71) Applicant: Regulus Therapeutics Inc., San Diego, CA (US)

(72) Inventors: Charles R. Allerson, San Diego, CA (US); Steven S. Neben, Del Mar, CA (US); Timothy Wright, San Diego, CA (US)

(73) Assignee: Regulus Therapeutics Inc., San Diego, CA (US)

( * ) Notice: Subject to any disclaimer, the term of this patent is extended or adjusted under 35 U.S.C. 154(b) by 816 days.

(21) Appl. No.: 17/052,333

(22) PCT Filed: May 7, 2019

(86) PCT No.: PCT/US2019/031044
§ 371 (c)(1),
(2) Date: Nov. 2, 2020

(87) PCT Pub. No.: WO2019/217369
PCT Pub. Date: Nov. 14, 2019

(65) Prior Publication Data
US 2021/0170034 A1    Jun. 10, 2021

Related U.S. Application Data

(60) Provisional application No. 62/668,467, filed on May 8, 2018.

(51) Int. Cl.
| | | |
|---|---|---|
| A61K 47/54 | (2017.01) | |
| A61K 31/439 | (2006.01) | |
| A61K 31/7072 | (2006.01) | |
| A61K 31/7088 | (2006.01) | |
| A61P 31/14 | (2006.01) | |

(52) U.S. Cl.
CPC .......... *A61K 47/549* (2017.08); *A61K 31/439* (2013.01); *A61K 31/7072* (2013.01); *A61K 31/7088* (2013.01); *A61P 31/14* (2018.01)

(58) Field of Classification Search
CPC ................ A61K 47/549; A61K 31/439; A61K 31/7072; A61K 31/7088; A61P 31/14
See application file for complete search history.

(56) References Cited

U.S. PATENT DOCUMENTS

| | | | |
|---|---|---|---|
| 5,994,517 A | 11/1999 | Ts'o et al. | |
| 6,300,319 B1 | 10/2001 | Manoharan | |
| 6,906,182 B2 | 6/2005 | Ts'o et al. | |
| 7,491,805 B2 | 2/2009 | Vargeese et al. | |
| 8,106,022 B2 | 1/2012 | Manoharan et al. | |
| 8,129,515 B2 | 3/2012 | Esau et al. | |
| 8,163,708 B2 | 4/2012 | Elmén et al. | |
| 8,288,356 B2 | 10/2012 | Obad et al. | |
| 8,313,772 B2 | 11/2012 | Rozema et al. | |
| 8,361,980 B2 | 1/2013 | Kauppinen et al. | |
| 8,404,659 B2 | 3/2013 | Kauppinen et al. | |
| 8,426,554 B2 | 4/2013 | Rozema et al. | |
| 8,450,467 B2 | 5/2013 | Manoharan et al. | |
| 8,828,956 B2 | 9/2014 | Manoharan et al. | |
| 9,157,083 B2 | 10/2015 | Bhat et al. | |
| 9,309,513 B2 | 4/2016 | Bhat et al. | |
| 9,506,030 B2 | 11/2016 | Bhat | |
| 9,574,194 B2 | 2/2017 | Bhat et al. | |
| 10,150,967 B2 | 12/2018 | Bhat et al. | |
| 10,240,151 B2 | 3/2019 | Bhat | |
| 10,941,400 B2 | 3/2021 | Bhat | |
| 2006/0148740 A1 | 7/2006 | Platenburg | |
| 2007/0049547 A1 | 3/2007 | Esau et al. | |
| 2009/0203132 A1 | 8/2009 | Swayze et al. | |
| 2010/0183639 A1 | 7/2010 | Uhlmann et al. | |
| 2010/0222413 A1 | 9/2010 | Stoffel et al. | |
| 2010/0298410 A1 | 11/2010 | Obad et al. | |
| 2010/0330035 A1 | 12/2010 | Hildebrandt-Eriksen et al. | |
| 2011/0077288 A1 | 3/2011 | Kauppinen et al. | |
| 2011/0243880 A1 | 10/2011 | Yurkovetskiy et al. | |
| 2012/0083596 A1 | 4/2012 | Elmén et al. | |
| 2012/0122801 A1 | 5/2012 | Platenburg | |
| 2012/0136042 A1 | 5/2012 | Manoharan et al. | |
| 2012/0157509 A1 | 6/2012 | Hadwiger et al. | |
| 2012/0238618 A1 | 9/2012 | Elmén et al. | |

(Continued)

FOREIGN PATENT DOCUMENTS

| | | |
|---|---|---|
| CN | 1344803 A | 4/2002 |
| EP | 2992095 A2 | 3/2016 |

(Continued)

OTHER PUBLICATIONS

Regulus Press Release, "Regulus to Present Updated Data Supporting RG-101 as Novel microRNA Therapeutic for the Treatment of HCV at the Liver Meeting® 2015 (AASLD)," Oct. 2, 2015, 2 pages.

(Continued)

*Primary Examiner* — Rebecca L Anderson
(74) *Attorney, Agent, or Firm* — McNeill Baur PLLC

(57) ABSTRACT

Described herein are compositions and methods for the inhibition of miR-122 activity. The compositions have certain nucleoside modifications that yield potent inhibitors of miR-122 activity and comprise moieties that facilitate delivery to the liver. The compositions may be administered to subjects infected with hepatitis C virus, as a treatment for hepatitis C virus and related conditions.

22 Claims, 1 Drawing Sheet
Specification includes a Sequence Listing.

(56) References Cited

U.S. PATENT DOCUMENTS

| | | |
|---|---|---|
| 2012/0270928 A1 | 10/2012 | Bhat |
| 2013/0178512 A1 | 7/2013 | Manoharan et al. |
| 2014/0127159 A1 | 5/2014 | Hodges |
| 2014/0248611 A1 | 9/2014 | Ichikawa et al. |
| 2014/0350090 A1 | 11/2014 | Bhat et al. |
| 2015/0018540 A1 | 1/2015 | Prakash et al. |
| 2015/0031130 A1 | 1/2015 | Bhat |
| 2015/0105449 A1 | 4/2015 | Bhat et al. |
| 2016/0251657 A1 | 9/2016 | Bhat et al. |
| 2017/0096668 A1 | 4/2017 | Bhat |

FOREIGN PATENT DOCUMENTS

| | | | |
|---|---|---|---|
| WO | 9530746 | A1 | 11/1995 |
| WO | 0076554 | A1 | 12/2000 |
| WO | 0125248 | A2 | 4/2001 |
| WO | 0148190 | A2 | 7/2001 |
| WO | 2004094595 | A2 | 11/2004 |
| WO | 2005013901 | A2 | 2/2005 |
| WO | 2005061710 | A1 | 7/2005 |
| WO | 2005107816 | A2 | 11/2005 |
| WO | 2006069584 | A2 | 7/2006 |
| WO | 2006078217 | A1 | 7/2006 |
| WO | 2006078278 | A2 | 7/2006 |
| WO | 2006112872 | A2 | 10/2006 |
| WO | 2007021896 | A2 | 2/2007 |
| WO | 2007027775 | A2 | 3/2007 |
| WO | 2007027894 | A2 | 3/2007 |
| WO | 2007112753 | A2 | 10/2007 |
| WO | 2007112754 | A2 | 10/2007 |
| WO | 2008091703 | A2 | 7/2008 |
| WO | 2008132234 | A2 | 11/2008 |
| WO | 2009043353 | A2 | 4/2009 |
| WO | 2009068033 | A2 | 6/2009 |
| WO | 2009073809 | A2 | 6/2009 |
| WO | 2009091972 | A2 | 7/2009 |
| WO | 2010076248 | A1 | 7/2010 |
| WO | 2010122538 | A1 | 10/2010 |
| WO | 2010144485 | A1 | 12/2010 |
| WO | 2011047312 | A1 | 4/2011 |
| WO | 2011130458 | A2 | 10/2011 |
| WO | 2012007477 | A1 | 1/2012 |
| WO | 2012037254 | A1 | 3/2012 |
| WO | 2012083046 | A2 | 6/2012 |
| WO | 2012089352 | A1 | 7/2012 |
| WO | 2012175733 | A1 | 12/2012 |
| WO | 2013000855 | A1 | 1/2013 |
| WO | 2013000856 | A1 | 1/2013 |
| WO | 2013033230 | A1 | 3/2013 |
| WO | 2013068347 | A1 | 5/2013 |
| WO | 2013068348 | A1 | 5/2013 |
| WO | 2013192576 | A2 | 12/2013 |
| WO | 2014048441 | A1 | 4/2014 |
| WO | 2014076195 | A1 | 5/2014 |
| WO | 2014118267 | A1 | 8/2014 |
| WO | 2014118272 | A1 | 8/2014 |
| WO | 2014179445 | A1 | 11/2014 |
| WO | 2014179446 | A2 | 11/2014 |
| WO | 2014179620 | A1 | 11/2014 |

OTHER PUBLICATIONS

Regulus Press Release, "RG-101 Interim Analysis Shows 97% Response at 8 Week Follow-Up," Feb. 17, 2016, 3 pages.

Regulus Therapeutics Inc., "A Single Subcutaneous Dose of 2mg/kg of RG-101, Regulus' Wholly-Owned, GalNac-Conjugated anti-miR Targeting microRNA-122, Demonstrates 4.1 log10 Mean Viral Load Reduction as Monotherapy at Day 29 in Patients with Varied HCV Genotypes and Treatment History, " Press Release, Oct. 22, 2014, 3 pages.

Regulus Therapeutics Inc., "Late-Breaking Oral Presentation at The International Liver Congress™ (ILC 2015) HighlightsRG-101's Potent, Durable and Pan-Genotypic Effects in Diverse HCV Population," Press Release, Apr. 25, 2015, 3 pages.

Regulus Therapeutics Inc., "Positive Preclinical Profile of RG-101, a GalNAc-conjugated anti-miR Targeting microRNA-122, Supports Clinical Development for the Treatment of HCV," Press Release, Nov. 4, 2013, 2 pages.

Regulus Therapeutics Inc., "Regulus Provides Update on 'Road to the Clinic' Strategy and Reports First Quarter 2013 Financial Results and Recent Highlights," Press Release, May 14, 2013, 3 pages.

Regulus Therapeutics Inc., "Regulus to Present Late-Breaking, Expanded RG-101 Data Set for the Treatment of HCV at The International Liver Congress™ 2015 (ILC 2015)," Press Release, Apr. 9, 2015, 3 pages.

Regulus Therapeutics Inc., "RG-101 Human Proof-of-Concept," Presentation, Oct. 22, 2014, 23 pages.

Regulus Therapeutics Inc., "RG-101: A Potentially Disruptive Agent to the HCV Treatment Landscape," Presentation, Feb. 9, 2015, 18 pages.

Regulus Therapeutics Inc., "Targeting microRNAs and Biological Networks: An Innovative Approach to Treat Disease," Presentation, Tides Conference, May 15, 2013, 31 pages.

Zhu et al., "Targeted Delivery of siRNA to Hepatocytes and Hepatic Stellate Cells by Bioconjugation," Bioconjug Chem., 2010, 21:2119-2127.

Sliedregt et al., "Design and Synthesis of Novel Amphiphilic Dendritic Galactosides for Selective Targeting of Liposomes to the Hepatic Asialoglycoprotein Receptor," 1999, 42: 609-618.

Spinelli et al., "Glycoclusters on oligonucleotide and PNA scaffolds: synthesis and applications," Chem Soc Rev., 2013, 42:4557-4573.

Stelma et al., "A Single Dose of RG-101, a GalNAc-Conjugated Oligonucleotide Targeting miR-122, Results in Undetectable HCV-RNA Levels at Week 28 of Follow-up in Chronic Hepatitis C Patients, APASL 2016, 25th Conference of the Asian Pacific Association for the Study of the Liver, Oral Presentation," Feb. 20-24, 2016, 22 pages.

Stelma et al., "Treatment with anti-miRNA122 RG-101 results in decreased IP-10 in patients with chronic hepatitis C," APASL 2016, 25th Conference of the Asian Pacific Association for the Study of the Liver, Abstract O-003, Feb. 8, 2016, 1 page.

Stelma, et al., "A Single Dose of Anti-Mir122 Oligonucleotide RG-101 Results in a Less Activated Phenotype of NK Cells in Patients with Chronic Hepatitis C," Abstract, The International Liver Congress® EASL ISC 2016, Apr. 2016, 2 pages.

Stelma, et al., "A Single Dose of Anti-Mir122 Oligonucleotide RG-101 Results in a Less Activated Phenotype of NK Cells in Patients with Chronic Hepatitis C," Poster, The International Liver Congress® EASL ISC 2016, Apr. 14, 2016, 1 page.

Stelma, et al., "Treatment with the Anti-miRNA 122 Oligonucleotide RG-101 Results in a Decrease in IP-10 but Does Not Affect the Levels of Other Cyotkines in Patients with Chronic Hepatitis C," Poster, AASLD, Nov. 17, 2015, 1 page.

Stelma, et al., "Treatment with the Anti-miRNA 122 Oligonucleotide RG-101 Results in a Decrease in IP-10 but Does Not Affect the Levels of Other Cyotkines in Patients with Chronic Hepatitis C," Abstract, AASLD, Oct. 7, 2015, 1 page.

Tripathi et al., "The Nuclear-Retained Noncoding RNA MALAT1 Regulates Alternative Splicing by Modulating SR Splicing Factor Phosphorylation," Molecular Cell, 2010, 39:925-938.

Tyagi et al., "Molecular beacons: probes that fluoresce upon hybridization," Nat Biotechnol., 1996, 14:303-308.

Van Der Ree et al., "A Single Subcutaneous Dose of 2 mg/kg or 4 mg/kg of RG-101, a Galnac-Conjugated Oligonucleotide with Antagonist Activity against miR-122, Results in Significant Viral Load Reductions in Chronic Hepatitis C Patients," presentation at the European Association for the Study of the Liver 50th Annual "The International Liver Congress", Apr. 25, 2015, 20 pages.

Van Der Ree et al., "A Single Dose of RG-101, a GalNAc-Conjugated Oligonucleotide Targeting miR-122, Results in Undetectable HCV-RNA Levels at Week 28 of Follow-up in Chronic Hepatitis C Patients," APASL 2016, 25th Conference of the Asian Pacific Association for the Study of the Liver, Poster, Feb. 20-24, 2016, 1 page.

(56) References Cited

OTHER PUBLICATIONS

Van Der Ree et al., "A Single Dose of RG-101, a GalNAc-Conjugated Oligonucleotide Targeting miR-122, Results in Undetectable HCV-RNA Levels at Week 28 of Follow-up in Chronic Hepatitis C Patients," APASL 2016, 25th Conference of the Asian Pacific Association for the Study of the Liver, Abstract P-0144 Feb. 8, 2016, 1 page.
Van Der Ree, et al., "A Single Dose of RG-101, a GalNAc-Conjugated Oligonucleotide Targeting miR-122, Results in Undetectable HCV RNA Levels in Chronic Hepatitis C Patients at Week 28 Follow-Up," Abstract, AASLD, Oct. 7, 2015, 2 pages.
Van Der Ree, et al., "A Single Dose of RG-101, a GalNAc-Conjugated Oligonucleotide Targeting miR-122, Results in Undetectable HCV RNA Levels in Chronic Hepatitis C Patients at Week 28 Follow-Up," Oral Presentation, The Liver Meeting®, the 66th Annual Meeting of the American Association for the Study of Liver Disease (AASLD), Nov. 17, 2015, 18 pages.
Van Der Ree, et al., "Sequence Analysis for Resistance Monitoring Following a Single Dose of RG-101, an Anti-miR Targeting Microma-122, in Chronic Hepatitis C Patients," The International Liver Congress® 2016 EASL ISC Apr. 14, 2016, 2016, 1 page.
Van Der Ree, et al., "Sequence Analysis for Resistance Monitoring Following a Single Dose of RG-101, an Anti-miR Targeting Microrna-122, in Chronic Hepatitis C Patients," The International Liver Congress® 2016 EASL ISC 2016, Apr. 2016, 1 page.
Van Rooij et al., "Developing MicroRNA Therapeutics," Circ Res., 2012, 110:496-507.
Xanthopoulos, Transcript of Oral Presentation, 12th Annual Needham Healthcare Conference, May 1, 2013, 9 pages.
Zatsepin et al., "Synthesis and Applications of Oligonucleotide—Carbohydrate Conjugate," Chemistry & Biodiversity, Helvetica Chimica Acta, 2004, 1(10):1413-1415.
Zheng et al., "Distribution and anti-HBV effects of antisense oligodeoxynucleotides conjugated to galactosylated poly-L-lysine," World J Gastroenterol., 2003, 9:1251-1255.
Zhu et al., "Site-specific delivery of oligonucleotides to hepatocytes after systemic administration," Bioconjug Chem, 2008, 19:290-298.
Bhat et al., "RG-101, a GalNAC-conjugated anti-miR employing a unique mechanism of action by targeting host factor microRNA-122 (miR-122), demonstrates potent activity and reduction of HCV in preclinical studies," AASLD Abstracts, Abstract #LB-28, Hepatology, 2013, 58:1393A.
Bhat et al., "RG-101, a GalNAC-conjugated anti-miR employing a unique mechanism of action by targeting host factor microRNA-122 (miR-122), demonstrates potent activity and reduction of HCV in preclinical studies," 64th Annual Meeting AASLD, Washington D.C. Nov. 3, 2013, 1 page.
Biessen et al., "Targeted delivery of oligodeoxynucleotides to parenchymal liver cells in vivo," Biochem. J., 1999, 340: 783-792.
Biton et al., "DNA photocleavage by DNA and DNA-LNA amino acid-dye conjugates," Bioconjug Chem., 2010, 21:616-621, includes supplemental data, (7 pages).
Duff et al., "Intrabody-Specific Delivery of Antisense Conjugates in Animals: Ligand-Linker-Antisense Oligomer Conjugates," Methods Enzymol., 2000, 313: 297-321.
Fabani et al., "miR-122 targeting with LNA/2'-O-methyl oligonucleotide mixmers, peptide nucleic acids (PNA), and PNA-peptide conjugates," RNA, 2008, 14:336-346.
File History of U.S. Appl. No. 14/266, 136, filed Apr. 30, 2014.
File History of U.S. Appl. No. 14/577,481, filed Dec. 19, 2014.
File History of U.S. Appl. No. 15/056,534, filed Feb. 29, 2016.
File History of U.S. Appl. No. 15/403,672, filed Jan. 11, 2017.
File History of U.S. Appl. No. 16/170,312, filed Oct. 25, 2018.
File History of U.S. Appl. No. 17/072,919, filed Oct. 16, 2020.
Gagnon et al., "Antisense and antigene inhibition of gene expression by cell-permeable oligonucleotide-obligospermine conjugates," J Am Chem Soc., 2011, 133:8404-8407.
Gibson et al., "Targeting microRNAs and Biological Networks: An Innovative Approach to Treat Disease," Presentation, Tides Conference, May 15, 2013, 31 pages.
Godeau et al., "Lipid-conjugated oligonucleotides via "click chemistry" efficiently inhibit hepatitis C virus translation," J Med Chem., 2008, 51:4374-4376, includes supplemental data (19 pages).
Grint, "RG-101, a Novel microRNA Therapeutic to Target the Host Factor of HCV," Oral Presentation, HepDART 2015, Dec. 8, 2015, 18 pages.
Hangeland et al., "Cell-Type Specific and Ligand Specific Enhancement of Cellular Uptake of Oligodeoxynucleoside-Methylphosphonates Covalently Linked with a Neoglycopeptide, YEE(ah-Ga1NAc)3," Bioconjug Chem., 1995, 6:695-701.
Haussecker et al., "miR-122 Continues to Blaze the Trail for MicroRNA Therapeutics," Molecular Therapy, 2010, 18:240-242.
Hogan et al., "Anti-miRs Competitively Inhibit microRNAs in Argonaute Complexes," PLoS One, 2014, 9:e100951, 11 pages.
Horvath, et al., "RG-101 in Combination with 4 Weeks of Oral Direct Acting Antiviral Therapy Achieves High Virologic Response Rates in Treatment Naïve Genotype 1 and 4 Chronic Hepatitis C Patients; Interim Results from a Randomised, Multi-Center, Phase 2 Study," Abstract, The International Liver Congress® EASL ISC 2016, Apr. 2016, 1 page.
Horvath, et al., "RG-101 in Combination with 4 Weeks of Oral Directing Acting Antiviral Therapy Achieves High Virologic Response Rates in Treatment Naïve Genotype 1 and 4 Chronic Hepatitis C Patients: Interim Results from Randomised, Multi-Center, Phase 2 Study," Oral Presentation, The International Liver Congress® EASL ISC 2016, Apr. 15, 2016, 16 pages.
Horwich et al., "Design and delivery of antisense oligonucleotides to block microRNA function in cultured Drosophila and human cells," Nature Protocols, 2008, 3:1537-1549.
International Search Report and Written Opinion for PCT/US2014/036137, mailed Dec. 15, 2014, 20 pages.
International Search Report and Written Opinion received in PCT/US2019/031044, dated Aug. 30, 2019, 17 pages.
Janssen et al., "Treatment of HCV Infection by Targeting MicroRNA," NEJM, 2013, 368:1685-1694.
Jopling, "Targeting microRNA-122 to Treat Hepatitis C Virus Infection," Viruses, 2010, 2:1382-1393.
Karskela et al., "Synthesis of Cellular Uptake of Fluorescently Labeled Multivalent Hyaluronan Disaccharide Conjugates of Oligonucleotide Phosphorothioates," Bioconjugate Chem., 2008, 19:2549-2558.
Katajisto et al., "Solid-Phase Synthesis of Multiantennary Oligonucleotide Glycoconjugates Utilizing On-Support Oximation," Bioconjugate Chem., 2004, 15:890-896.
Lehmann et al., "Synthesis and properties of bile acid phosphoramidites 5'-tethered to antisense bligodeoxynucleotides against HCV," Bioorg Med Chem., 2001, 9:1827-1835.
Lennox et al., "Chemical Modification and Design of Anti-miRNA Oligonucleotides," Gene Ther., 2011, 18 (12):1111-20.
Leriche et al., "Cleavable linkers in chemical biology," Bioorg Med Chem., 2012, 20:571-582.
Liu et al., "Pharmacokinetics and Pharmacology of RG-101, a Novel Galnac-conjugated Oligonucleotide Targeting MicroRNA-122, in Healthy Volunteers," poster presented at the European Association for the Study of the Liver 50th Annual "The International Liver Congress", Apr. 25, 2015, 1 page.
Maier et al., "Synthesis of Antisense Oligonucleotides Conjugated to a Multivalent Carbohydrate Cluster for Cellular Targeting," Bioconjugate Chem., 2003, 14:18-29.
Makino et al., "Intravenous injection with antisense oligodeoxynucleotides against angiotensinogen decreases blood pressure in spontaneously hypertensive rats," Hypertension, 1998, 31:1166-1170.
Manoharan, "Oligonucleotide Conjugates as Potential Antisense Drugs with Improved Uptake, Biodistribution, Targeted Delivery, and Mechanism of Action," Antisense Nucl. Acid Drug Develop., 2002, 12:103-128.
Merwin et al., "Targeted Delivery of DNA Using YEE(GalNAcAH)3, a Synthetic Glycopeptide Ligand for the Asialoglycoprotein Receptor," Bioconjug Chem., 1994, 5:612-620.
Neben et al., "Pharmacokinetics, Pharmacodynamics, and Toxicity Profile of RG-101, a Novel Galnac-conjugated Hepatocyte-targeting Inhibitor of MicroRNA-122, in Rodents and Cynomolgus

(56) References Cited

OTHER PUBLICATIONS

Monkeys," poster presented at the European Association for the Study of the Liver 50th Annual "The International Liver Congress", Apr. 25, 2015, 1 page.

Neben et al., "RG-101, a Novel Galnac-conjugated Inhibitor of MicroRNA-122, Demonstrates Significant Viral Load Reduction and Reduces Liver Steatosis in Human Chimeric Mice Infected with Genotype 1A or Hard-to-treat Genotype 3A Hepatitis C Virus (HCV)," poster presented at the European Association for the Study of the Liver 50th Annual "The International Liver Congress", Apr. 25, 2015, 1 page.

Neben, et al., "RG-101 Demonstrates Favorable In Vitro Antiviral Activity and Cross Resistance Profile to Support Clinical Combination Studies in HCV Patients," Abstract, The International Liver Congress® EASL ISC 2016, Apr. 2016, 1 page.

Neben, et al., "RG-101 Demonstrates Favorable In Vitro Antiviral Activity and Cross Resistance Profile to Support Clinical Combination Studies in HCV Patients," Poster, The International Liver Congress® EASL ISC 2016, Apr. 14, 2016, 1 page.

Patrick, et al., "Genotype and Phenotype Characterization of HCV Variants from a Phase I Trial of RG-101, a GalNAc-Conjugated Oligonucleotide Targeting Microma-122, in Patients with Chronic HCV Infection," Poster, International Conference on Antiviral Research (ICAR), Apr. 18, 2016, 1 page.

Rajur et al., "Covalent protein-oligonucleotide conjugates for efficient delivery of antisense molecules," Bioconjug Chem., 1997, 8:935-940.

Raouane et al., "Synthesis, characterization, and in vivo delivery of siRNA-squalene nanoparticles targeting fusion oncogene in papillary thyroid carcinoma," J Med Chem, 2011, 54:4067-4076, includes supplemental data (10 pages).

Regulus Presentation, "RG-101, a Novel microRNA Therapeutic to Target the Host Factor of HCV," Interim Phase II Results Webcast and Conference Call, Feb. 17, 2016, 11 pages.

Regulus Press Release, "Regulus Completes RG-101 Enrollment in Phase II Combination Therapy," Jan. 21, 2016, 3 pages.

Regulus Press Release, "Regulus Presents Additional Interim Data on RG-101 at International Liver Congress® (ILC 2016)," Apr. 15, 2016, 3 pages.

Regulus Press Release, "Regulus Provides Update on Clinical Hold of RG-101," Jul. 27, 2016, 2 pages.

Regulus Press Release, "Regulus Reports Clinical Hold of RG-101," Jun. 27, 2016, 2 pages.

Regulus Press Release, "Regulus Reports Positive Top-Line Data," Jun. 7, 2016, 3 pages.

Regulus Press Release, "Regulus to Present New RG-101 Data at The International Liver Congress® 2016 (ILC 2016)," Mar. 16, 2016, 3 pages.

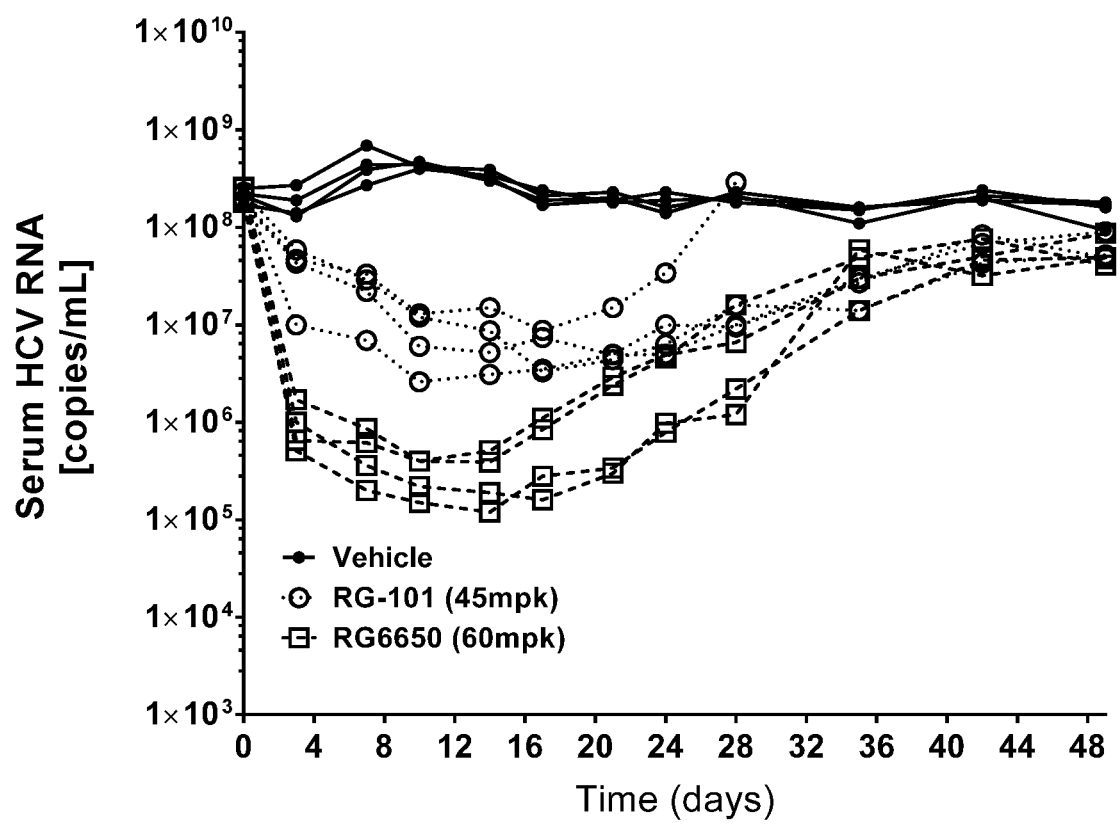

GALNAC CONJUGATED MODIFIED OLIGONUCLEOTIDES AS miR-122 INHIBITOR HAVING HCV ANTIVIRAL ACTIVITY WITH REDUCED HYPERBILIRUBINEMIA SIDE-EFFECT

CROSS-REFERENCE TO RELATED APPLICATIONS

This application is a national stage application of International Application No. PCT/US2019/031044, filed May 7, 2019, which claims the benefit of priority of U.S. Provisional Application No. 62/668,467, filed May 8, 2018.

FIELD OF INVENTION

Provided herein are compounds and methods for use in modulating the activity of miR-122. Such methods comprise treatment of diseases related to miR-122 activity, such HCV infection.

DESCRIPTION OF RELATED ART

MicroRNAs (microRNAs), also known as "mature microRNA" are small (approximately 18-24 nucleotides in length), non-coding RNA molecules encoded in the genomes of plants and animals. In certain instances, highly conserved, endogenously expressed microRNAs regulate the expression of genes by binding to the 3'-untranslated regions (3'-UTR) of specific mRNAs. More than 1000 different microRNAs have been identified in plants and animals. Certain mature microRNAs appear to originate from long endogenous primary microRNA transcripts (also known as pri-microRNAs, pri-mirs, pri-miRs or pri-pre-microRNAs) that are often hundreds of nucleotides in length (Lee, et al., EMBO J., 2002, 21(17), 4663-4670).

miR-122, a microRNA abundantly and specifically expressed in the liver, is a critical host factor for hepatitis C virus accumulation (Jopling et al., Science. 2005, 309 (5740):1577-81). miR-122 interacts with HCV by binding to two closely spaced seed sequence sites in the 5' non-coding region of the HCV genome, resulting in stabilization of the HCV genome, supporting replication and translation (Jangra et al., J Virol., 2010, 84:6615-6625; Machlin, et al., 2011). Importantly, the miR-122 binding sites are completely conserved in the HCV genome across all genotypes and subtypes (Wilson et al., J. Virol., 2011, 85:2342-2350). Inhibition of miR-122 with anti-miR results in reduced total circulating cholesterol levels in mice and cynomolgus monkey, as well as changes in the expression of genes involved in cholesterol homeostasis, fatty acid, and lipid metabolism (Esau et al., 2006, Cell Metabolism, 3:87-98). In chronic treatment naïve HCV infected subjects, miravirsen, an LNA-modified anti-miR-122 oligonucleotide, led to a reduction in serum HCV RNA (Janssen et al., N Engl J Med., 2013, 368:1685-1694). A single administration of RG-101, a hepatocyte-targeted anti-miR-122 compound, was well tolerated and resulted in substantial viral load reduction in HCV-infected subjects (van der Ree et al., 2017, Lancet, 389 (10070):709-717).

Although current direct-acting antivirals are achieving high rates of sustained viral response, there is an underserved population of HCV-infected subjects who do not respond to current treatments, or who relapse following successful treatment. Resistance to antiviral therapy is a major problem associated with a high mutation rate of HCV and is seen even with combinations of drugs. Additionally, poor subject compliance with treatment regimens requiring at least once daily adminstrations of oral agents for extended periods (e.g. 12 weeks for Harvoni®) may interfere with achieving a high response rate. Accordingly, therapeutics that target conserved, mutation-resistant viral host factors, such as miR-122, represent an opportunity to effect higher and more durable cure rates.

SUMMARY OF INVENTION

Embodiment 1. A compound of the structure:

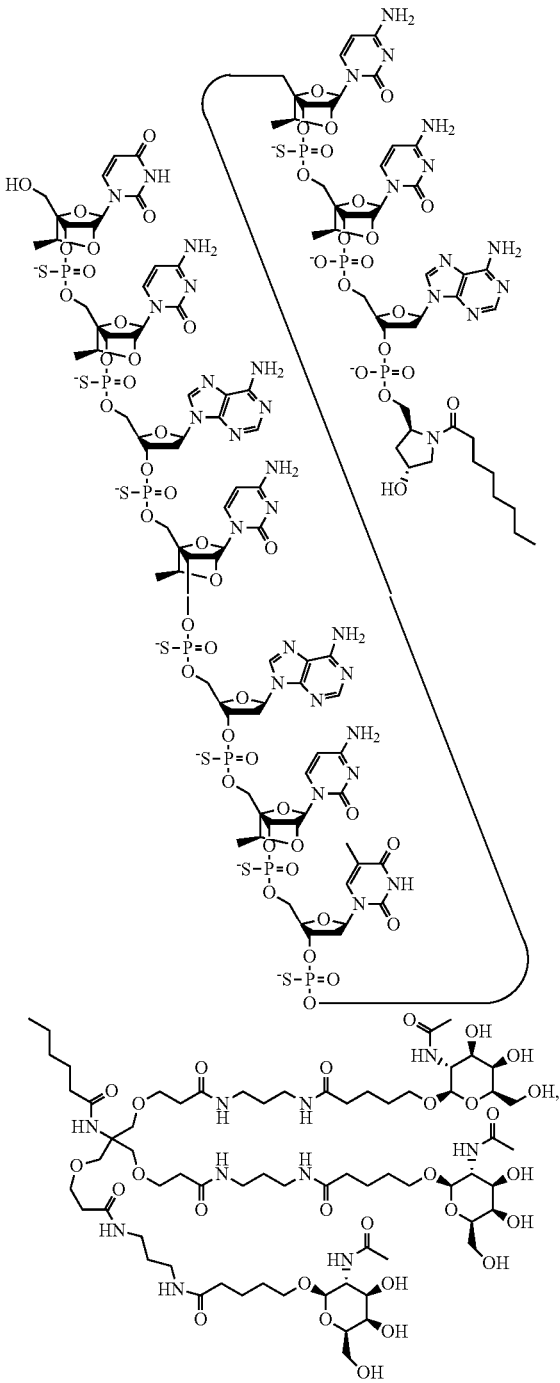

or a pharmaceutically acceptable salt thereof.

Embodiment 2. The compound of embodiment 1, which is a pharmaceutically acceptable salt of the structure.

Embodiment 3. The compound of embodiment 2, which is a sodium salt of the structure.

Embodiment 4. A pharmaceutical composition comprising a compound of any one of embodiments 1 to 3 and a pharmaceutically acceptable diluent.

Embodiment 5. The pharmaceutical composition of embodiment 4, wherein the pharmaceutically acceptable diluent is an aqueous solution.

Embodiment 6. The pharmaceutical composition of embodiment 5, wherein the aqueous solution is a saline solution.

Embodiment 7. A pharmaceutical composition comprising a compound of any one of embodiments 1 to 3, which is a lyophilized composition.

Embodiment 8. A pharmaceutical composition consisting essentially of a compound of any one of embodiments 1 to 3 in a saline solution.

Embodiment 9. A method of inhibiting the activity of miR-122 in a cell comprising contacting a cell with a compound of one any one of embodiments 1 to 3.

Embodiment 10. The method of embodiment 9, wherein the cell is in vivo.

Embodiment 11. The method of embodiment 9, wherein the cell is in vitro.

Embodiment 12. A method of treating HCV infection comprising administering to an HCV-infected subject at least one dose of a compound of any one of embodiments 1 to 3, or a pharmaceutical composition of any one of embodiments 4 to 8.

Embodiment 13. A method of treating hepatitis C virus (HCV) infection comprising administering at least one dose of a compound of any one of embodiments 1 to 3, or a pharmaceutical composition of any one of embodiments 4 to 8 and at least one direct-acting antiviral (DAA) to an HCV-infected subject during a treatment period, wherein the duration of the treatment period is 12 weeks or less, and wherein a start dose of the compound or pharmaceutical composition is administered at the start of the treatment period and an end dose of the compound or pharmaceutical composition is administered at the end of the treatment period.

Embodiment 14. The method of embodiment 13, wherein the start dose and the end dose are the only doses of the compound or pharmaceutical composition administered during the treatment period.

Embodiment 15. A method of treating hepatitis C virus (HCV) infection comprising administering at least one dose of a compound of any one of embodiments 1 to 3, or a pharmaceutical composition of any one of embodiments 4 to 8 and at least one direct-acting antiviral (DAA) to an HCV-infected subject during a treatment period, wherein the duration of the treatment period is 12 weeks or less, and wherein a start dose of the compound or pharmaceutical composition is administered at the start of the treatment period, and the start dose is the only dose of the compound or pharmaceutical composition administered during the treatment period.

Embodiment 16. A method of treating hepatitis C virus (HCV) infection comprising administering at least one dose of a compound of any one of embodiments 1 to 3, or a pharmaceutical composition of any one of embodiments 4 to 8 and at least one direct-acting antiviral (DAA) to an HCV-infected subject during a treatment period, wherein the duration of the treatment period is 12 weeks or less, and wherein an end dose of the compound or pharmaceutical composition is administered at the end of the treatment period, and the end dose is the only dose of the compound or pharmaceutical composition administered during the treatment period.

Embodiment 17. The method of any one of embodiments 13 to 16, wherein the duration of the treatment period is 2 to 10 weeks, 4 to 8 weeks, 2 to 6 weeks, or 1 to 4 weeks.

Embodiment 18. The method of any one of embodiments 13 to 16, wherein the duration of the treatment period is 11 weeks, 10 weeks, 9 weeks, 8 weeks, 7 weeks, 6 weeks, 5 weeks, 4 weeks, 3 weeks, 2 weeks, or 1 week.

Embodiment 19. The method of any one of embodiments 13 to 16, wherein the duration of the treatment period is 26, 27, 28, 29, or 30 days.

Embodiment 20. The method of any one of embodiments 13 to 16, wherein the duration of the treatment period is 28 or 29 days.

Embodiment 21. The method of any one of embodiments 13 to 16, wherein the duration of the treatment period is 18, 19, 20, 21, or 22 days.

Embodiment 22. The method of any one of embodiments 13 to 16, wherein the duration of the treatment period is 21 or 22 days.

Embodiment 23. The method of any one of embodiments 13 to 16, wherein the duration of the treatment period is 12, 13, 14, 15, or 16 days.

Embodiment 24. The method of any one of embodiments 13 to 16, wherein the duration of the treatment period is 14 or 15 days.

Embodiment 25. The method of any one of embodiments 13 to 16, wherein the duration of the treatment period is 6, 7, 8, or 9 days.

Embodiment 26. The method of any one of embodiments 13 to 16, wherein the duration of the treatment period is 7 or 8 days.

Embodiment 27. The method of any one of embodiments 13 to 15 or 17 to 26, wherein the start dose of the compound or pharmaceutical composition and the first dose of the DAA are administered within seven days of each other.

Embodiment 28. The method of any one of embodiments 13 to 15 or 17 to 26, wherein the start dose of the compound or pharmaceutical composition is administered one day before the first dose of the DAA.

Embodiment 29. The method of any one of embodiments 13 to 15 or 17 to 26, wherein the start dose of the compound or pharmaceutical composition is administered on the same day as the first dose of the DAA.

Embodiment 30. The method of any one of embodiments 13 to 15 or 17 to 26, wherein the start dose of the compound or pharmaceutical composition is administered one day after the first dose of the DAA.

Embodiment 31. The method of any one of embodiments 13, 14 or 16 to 26, wherein the end dose of the compound or pharmaceutical composition and the last dose of the DAA are administered within 7 days of each other.

Embodiment 32. The method of any one of embodiments 13, 14 or 16 to 26, wherein the end dose of the compound or pharmaceutical composition is administered one day prior to the last dose of the DAA.

Embodiment 33. The method of any one of embodiments 13, 14 or 16 to 26, wherein the end dose of the compound or pharmaceutical composition is administered on the same day as the last dose of the DAA.

Embodiment 34. The method of any one of embodiments 13, 14 or 16 to 26, wherein the end dose of the compound or pharmaceutical composition is administered on the day after the last dose of the DAA.

Embodiment 35. The method of any one of embodiments 12 to 34, where in the HCV-infected subject is infected with genotype 1.

Embodiment 36. The method of embodiment 35, wherein the HCV-infected subject is infected with genotype 1a.

Embodiment 37. The method of embodiment 35, wherein the HCV-infected subject is infected with genotype 1b.

Embodiment 38. The method of any one of embodiments 12 to 34, wherein the HCV-infected subject is infected with genotype 2.

Embodiment 39. The method of any one of embodiments 12 to 34, wherein the HCV-infected subject is infected with genotype 3.

Embodiment 40. The method of any one of embodiments 12 to 34, wherein the HCV-infected subject is infected with genotype 4.

Embodiment 41. The method of any one of embodiments 12 to 34, wherein the HCV-infected subject is infected with genotype 5.

Embodiment 42. The method of any one of embodiments 12 to 34, wherein the HCV-infected subject is infected with genotype 6.

Embodiment 43. The method of any one of embodiments 12 to 42, wherein the HCV-infected subject is determined to be infected with an HCV having one or more resistance-associated polymorphisms.

Embodiment 44. The method of any one of embodiments 12 to 43, wherein the HCV-infected subject is a treatment-naïve subject.

Embodiment 45. The method of any one of embodiments 12 to 44, wherein the HCV-infected subject has an HCV-associated disease.

Embodiment 46. The method of embodiment 45, wherein the HCV-associated disease is cirrhosis, liver fibrosis, steatohepatitis, steatosis, or hepatocellular carcinoma.

Embodiment 47. The method of any one of embodiments 12 to 46, wherein the HCV-infected subject is an HCV-infected subject with renal impairment.

Embodiment 48. The method of any one of embodiments 12 to 47, wherein the HCV-infected subject is and HCV/HIV co-infected subject.

Embodiment 49. The method of any one of embodiments 12 to 48, wherein the administering achieves a sustained viral response.

Embodiment 50. The method of any of embodiments 13 to 49, wherein the HCV RNA level is below a lower limit of quantitation (LLOQ) at the end of the treatment period or at a time point after the end of the treatment period.

Embodiment 51. The method of embodiment 50, wherein the HCV RNA level below the LLOQ at 4 weeks after the end of the treatment period.

Embodiment 52. The method of embodiment 50 or embodiment 51, wherein the HCV RNA level is below the LLOQ at 8 weeks after the end of the treatment period.

Embodiment 53. The method of any one of embodiments 50 to 52, wherein the HCV RNA level is below the LLOQ at 12 weeks after the end of the treatment period.

Embodiment 54. The method of any one of embodiments 50 to 53, wherein the HCV RNA level is below the LLOQ at 24 weeks after the end of the treatment period.

Embodiment 55. The method of any one of embodiments 50 to 54, wherein the HCV RNA level is below the LLOQ at 36 weeks after the end of the treatment period.

Embodiment 56. The method of any one of embodiments 50 to 55, wherein the HCV RNA level is below the LLOQ at 48 weeks after the end of the treatment period.

Embodiment 57. The method of any one of embodiments 50 to 56, wherein the LLOQ is 25 IU/mL.

Embodiment 58. The method of any one of embodiments 50 to 56, wherein the LLOQ is 15 IU/mL.

Embodiment 59. The method of any one of embodiments 50 to 56, wherein the LLOQ is 12 IU/mL.

Embodiment 60. The method of any one of embodiments 50 to 59, wherein the HCV RNA level is quantitated using a real-time polymerase chain reaction-based assay.

Embodiment 61. The method of any one of embodiments 13 to 60, wherein the DAA is administered daily.

Embodiment 62. The method of any of embodiments 13 to 61, wherein the DAA is selected from a protease inhibitor, a nucleoside polymerase inhibitor, a nucleotide polymerase inhibitor, a non-nucleoside polymerase inhibitor, an NS3B inhibitor, an NS3/4A inhibitor, an NS4A inhibitor, an NS5A inhibitor, an NS5B inhibitor, and a cyclophilin inhibitor.

Embodiment 63. The method of any of embodiments 13 to 62, wherein the DAA is selected from one or more of sofosbuvir, ledipasvir, ombitasvir, dasabuvir, glecaprevir, pibrentasvir, elbasvir, grazoprevir, ribavirin, ombitasvir, paritaprevir, ritonavir, boceprevir, vaniprevir, asunaprevir, daclatasvir, simeprevir, mericitabine, tegobuvir, danoprevir, sovaprevir, voxilaprevir, velpatasvir, and GSK2878175.

Embodiment 64. The method of any one of embodiments 13 to 63, wherein the at least one DAA comprises sofosbuvir.

Embodiment 65. The method of any one of embodiments 13 to 64, wherein the at least one DAA comprises ledipasvir and sofosbuvir.

Embodiment 66. The method of any one of embodiments 12 to 65 wherein the dose of the compound is less than or equal to 4.0 mg/kg, less than or equal to 3.5 mg/kg, less than or equal to 3.0 mg/kg, less than or equal to 2.5 mg/kg, less than or equal to 2.0 mg/kg, less than or equal to 1.5 mg/kg, less than or equal to 1.0 mg/kg, or less than or equal to 0.5 mg/kg.

Embodiment 67. A compound of any one of embodiments 1 to 3, or a pharmaceutical composition of any one of embodiments 4 to 8, for use in therapy.

Embodiment 68. A compound of any one of embodiments 1 to 3, or a pharmaceutical composition of any one of embodiments 4 to 8, for use in treating an HCV-infected subject.

BRIEF DESCRIPTION OF DRAWINGS

FIG. 1. Reduction of HCV RNA in serum of HCV-infected mouse model following treatment with PBS, RG-101, or RG6650.

DETAILED DESCRIPTION

Unless defined otherwise, all technical and scientific terms used herein have the same meaning as is commonly understood by one of skill in the arts to which the invention belongs. Unless specific definitions are provided, the nomenclature utilized in connection with, and the procedures and techniques of, analytical chemistry, synthetic organic chemistry, and medicinal and pharmaceutical chemistry described herein are those well known and commonly used in the art. In the event that there is a plurality of definitions for terms herein, those in this section prevail. Standard techniques may be used for chemical synthesis, chemical analysis, pharmaceutical preparation, formulation and delivery, and treatment of subjects. Certain such techniques and procedures may be found for example in "Carbohydrate Modifications in Antisense Research" Edited by Sangvi and Cook, American Chemical Society, Washington D.C., 1994; and "Remington's Pharmaceutical Sciences," Mack Publishing Co., Easton, Pa., 18th edition, 1990; and which is hereby incorporated by reference for any purpose. Where permitted, all patents, patent applications, published applications and publications, GENBANK sequences, websites and other published materials referred to throughout the entire disclosure herein, unless noted otherwise, are incorporated by reference in their entirety. Where reference is made to a URL or other such identifier or address, it is understood that such identifiers can change and particular information on the internet can change, but equivalent information can be found by searching the internet. Reference thereto evidences the availability and public dissemination of such information.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Definitions

"HCV infection" means infection with one or more genotypes of the Hepatitis C Virus.

"HCV-infected subject" means a subject who has been infected with one or more genotypes of the hepatitis C virus. An HCV-infected subject may or may not exhibit symptoms of HCV infection. HCV-infected subjects include subjects who have been infected with one or more genotypes of HCV, but HCV RNA in the blood of the subject is below detectable levels.

"Treatment-naïve HCV-infected subject" means an HCV-infected subject that has not received prior treatment for HCV infection.

"HCV-associated disease" means a pathological process that is mediated by HCV infection. HCV-associated diseases include, but are not limited to, cirrhosis, liver fibrosis, steatoheptatitis, and hepatocellular carcinoma.

"Blood HCV RNA" means hepatitis C virus RNA present in the blood of an HCV-infected subject. Blood includes whole blood and serum.

"Blood" means whole blood and blood fractions, such as serum and plasma.

"Rebound in serum HCV RNA" means an increase in HCV RNA level following a previous decrease in HCV RNA level.

"HCV RNA level" means the amount of HCV RNA in a given volume of the blood of a subject.

HCV RNA level may be expressed as copies of RNA per milliliter. "HCV RNA level" may also be called "HCV viral load" or "HCV RNA titer." HCV RNA level may be measured using an in vitro reverse transcription-polymerase chain reaction assay.

"Sustained virological response" means undetectable hepatitis C virus RNA in the blood of the subject at the end of an entire course of treatment and after a further 12 weeks. In certain embodiments, HCV RNA is considered undetectable below 40 copies per milliliter of blood.

"SVRX," wherein X is the number of weeks since the end of a treatment period, means a sustained virological response at that time point following the end of the treatment period. For example, SVR8 is a sustained virological response at 8 weeks following the end of the treatment period.

"Non-responder" means a subject who has received treatment but is not experiencing a clinically acceptable improvement in disease markers or symptoms.

"Interferon non-responder" means an HCV-infected subject who has received treatment with interferon, but is not experiencing a clinically acceptable reduction in HCV RNA level.

"Direct-acting anti-viral agent" or "DAA" means a pharmaceutical agent that inhibits the activity of HCV by interacting directly with a protein encoded by the HCV genome. A DAA may be an inhibitor of the NS3/4A protease, the NS5A non-structural protein, or the NS5B polymerase. A DAA may be a nucleoside compound, or a non-nucleoside compound.

"Direct-acting anti-viral non-responder" means an HCV-infected subject who has received treatment with a direct-acting anti-viral agent, but is not experiencing a clinically acceptable reduction in HCV RNA level. In certain embodiments, the virus has developed resistance to the direct-acting anti-viral agent.

"Renal impairment" means a condition in which the kidneys fail to adequately filter waste products from the blood. Renal impairment may be determined by estimated glomerular filtration rate, or measured glomerular filtration rate. Renal impairment may also be determined by creatinine clearance.

"miR-122-associated condition" means any disease, disorder or condition that can be treated, prevented or ameliorated by modulating miR-122. A miR-122-associated disease need not be characterized by excess miR-122. miR-122-associated diseases included, without limitation, HCV infection, elevated cholesterol, and iron overload disorders.

"Iron overload disorder" means any disease, disorder or condition characterized by excess iron in the body.

"Subject" means a human selected for treatment or therapy.

"Subject in need thereof" means a subject that is identified as in need of a therapy or treatment.

"Subject suspected of having" means a subject exhibiting one or more clinical indicators of a disease.

"Administering" means providing a pharmaceutical agent or composition to a subject, and includes, but is not limited to, administering by a medical professional and self-administering.

"Parenteral administration" means administration through injection or infusion. Parenteral administration includes, but is not limited to, subcutaneous administration, intravenous administration, and intramuscular administration.

"Subcutaneous administration" means administration just below the skin.

"Intravenous administration" means administration into a vein.

"Administered concomitantly" refers to the co-administration of two or more agents to a subject in any manner in which the pharmacological effects of each agent are present in a subject. Concomitant administration does not require that both agents be administered in a single pharmaceutical composition, in the same dosage form, or by the same route of administration. The effects of both agents need not be present at the same time. The effects need only be overlapping for a period of time and need not be coextensive.

"Duration" means the period of time during which an activity or event continues. In certain embodiments, the duration of treatment is the period of time during which doses of a pharmaceutical agent or pharmaceutical composition are administered.

"Therapy" means a disease treatment method. In certain embodiments, therapy includes, but is not limited to, chemotherapy, radiation therapy, or administration of a pharmaceutical agent.

"Treatment" means the application of one or more specific procedures used for the cure or amelioration of a disease. In certain embodiments, the specific procedure is the administration of one or more pharmaceutical agents.

"Amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"At risk for developing" means the state in which a subject is predisposed to developing a condition or disease. In certain embodiments, a subject at risk for developing a condition or disease exhibits one or more symptoms of the condition or disease, but does not exhibit a sufficient number of symptoms to be diagnosed with the condition or disease. In certain embodiments, a subject at risk for developing a condition or disease exhibits one or more symptoms of the condition or disease, but to a lesser extent required to be diagnosed with the condition or disease.

"Prevent the onset of" means to prevent the development of a condition or disease in a subject who is at risk for developing the disease or condition. In certain embodiments, a subject at risk for developing the disease or condition receives treatment similar to the treatment received by a subject who already has the disease or condition.

"Delay the onset of" means to delay the development of a condition or disease in a subject who is at risk for developing the disease or condition. In certain embodiments, a subject at risk for developing the disease or condition receives treatment similar to the treatment received by a subject who already has the disease or condition.

"Therapeutic agent" means a pharmaceutical agent used for the cure, amelioration or prevention of a disease.

"Dose" means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual. In certain embodiments, a dose is administered as a slow infusion.

"Dosage unit" means a form in which a pharmaceutical agent is provided. In certain embodiments, a dosage unit is a vial containing lyophilized oligonucleotide. In certain embodiments, a dosage unit is a vial containing reconstituted oligonucleotide.

"Therapeutically effective amount" refers to an amount of a pharmaceutical agent that provides a therapeutic benefit to an animal.

"Pharmaceutical composition" means a mixture of substances suitable for administering to an individual that includes a pharmaceutical agent. For example, a pharmaceutical composition may comprise a sterile aqueous solution.

"Pharmaceutical agent" means a substance that provides a therapeutic effect when administered to a subject.

"Active pharmaceutical ingredient" means the substance in a pharmaceutical composition that provides a desired effect.

"Pharmaceutically acceptable salt" means a physiologically and pharmaceutically acceptable salt of a compound provided herein, i.e., a salt that retains the desired biological activity of the compound and does not have undesired toxicological effects when administered to a subject. Non-limiting exemplary pharmaceutically acceptable salts of compounds provided herein include sodium and potassium salt forms. The terms "compound," "oligonucleotide," and "modified oligonucleotide" as used herein include pharmaceutically acceptable salts thereof unless specifically indicated otherwise.

"Saline solution" means a solution of sodium chloride in water.

"Improved organ function" means a change in organ function toward normal limits. In certain embodiments, organ function is assessed by measuring molecules found in a subject's blood or urine. For example, in certain embodiments, improved liver function is measured by a reduction in blood liver transaminase levels. In certain embodiments, improved kidney function is measured by a reduction in blood urea nitrogen, a reduction in proteinuria, a reduction in albuminuria, etc.

"Acceptable safety profile" means a pattern of side effects that is within clinically acceptable limits.

"Side effect" means a physiological response attributable to a treatment other than desired effects.

In certain embodiments, side effects include, without limitation, injection site reactions, liver function test abnormalities, renal function abnormalities, liver toxicity, renal toxicity, central nervous system abnormalities, and myopathies. Such side effects may be detected directly or indirectly. For example, increased aminotransferase levels in serum may indicate liver toxicity or liver function abnormality. For example, increased bilirubin may indicate liver toxicity or liver function abnormality.

"Injection site reaction" means inflammation or abnormal redness of skin at a site of injection in an individual.

"Subject compliance" means adherence to a recommended or prescribed therapy by a subject.

"Comply" means the adherence with a recommended therapy by a subject.

"Recommended therapy" means a treatment recommended by a medical professional to treat, ameliorate, delay, or prevent a disease.

"miR-122" means a microRNA having the nucleobase sequence (SEQ ID NO: 1)
UGGAGUGUGACAAUGGUGUUUG.

"Oligonucleotide" means a compound comprising a plurality of linked nucleosides, each of which can be modified or unmodified, independent from one another.

"Modified oligonucleotide" means a single-stranded oligonucleotide having one or more modifications relative to a naturally occurring terminus, sugar, nucleobase, and/or internucleoside linkage. A modified oligonucleotide may comprise unmodified nucleosides.

"Anti-miR" means a modified oligonucleotide having a nucleobase sequence complementary to a microRNA.

"Anti-miR-122" means a modified oligonucleotide having a nucleobase sequence complementary to miR-122. In certain embodiments, an anti-miR-122 is fully complementary to miR-122 (i.e., 100% complementary). In certain embodiments, an anti-miR-122 is at least 90%, at least 93%, at least 94%, at least 95%, or 100% complementary.

"Targeting" means the process of design and selection of nucleobase sequence that will hybridize to a target nucleic acid.

"Targeted to" means having a nucleobase sequence that will allow hybridization to a target nucleic acid.

"Modulation" means a perturbation of function, amount, or activity. In certain embodiments, modulation means an increase in function, amount, or activity. In certain embodiments, modulation means a decrease in function, amount, or activity.

"Expression" means any functions and steps by which a gene's coded information is converted into structures present and operating in a cell.

"Nucleobase sequence" means the order of contiguous nucleobases in an oligomeric compound or nucleic acid, typically listed in a 5' to 3' orientation, independent of any sugar, linkage, and/or nucleobase modification.

"Contiguous nucleobases" means nucleobases immediately adjacent to each other in a nucleic acid.

"Nucleobase complementarity" means the ability of two nucleobases to pair non-covalently via hydrogen bonding.

"Complementary" means that one nucleic acid is capable of hybridizing to another nucleic acid or oligonucleotide. In certain embodiments, complementary refers to an oligonucleotide capable of hybridizing to a target nucleic acid.

"Fully complementary" means each nucleobase of an oligonucleotide is capable of pairing with a nucleobase at each corresponding position in a target nucleic acid. In certain embodiments, an oligonucleotide is fully complementary (also referred to as 100% complementary) to a microRNA, i.e. each nucleobase of the oligonucleotide is complementary to a nucleobase at a corresponding position in the microRNA. A modified oligonucleotide may be fully complementary to a microRNA, and have a number of linked nucleosides that is less than the length of the microRNA. For example, an oligonucleotide with 10 linked nucleosides, where each nucleobase of the oligonucleotide is complementary to a nucleobase at a corresponding position in a microRNA, is fully complementary to the microRNA.

"Percent complementarity" means the percentage of nucleobases of an oligonucleotide that are complementary to an equal-length portion of a target nucleic acid. Percent complementarity is calculated by dividing the number of nucleobases of the oligonucleotide that are complementary to nucleobases at corresponding positions in the target nucleic acid by the total number of nucleobases in the oligonucleotide.

"Percent identity" means the number of nucleobases in a first nucleic acid that are identical to nucleobases at corresponding positions in a second nucleic acid, divided by the total number of nucleobases in the first nucleic acid. In certain embodiments, the first nucleic acid is a microRNA and the second nucleic acid is a microRNA. In certain embodiments, the first nucleic acid is an oligonucleotide and the second nucleic acid is an oligonucleotide.

"Hybridize" means the annealing of complementary nucleic acids that occurs through nucleobase complementarity.

"Mismatch" means a nucleobase of a first nucleic acid that is not capable of Watson-Crick pairing with a nucleobase at a corresponding position of a second nucleic acid.

"Identical" in the context of nucleobase sequences, means having the same nucleobase sequence, independent of sugar, linkage, and/or nucleobase modifications and independent of the methyl state of any pyrimidines present.

"MicroRNA" means an endogenous non-coding RNA between 18 and 25 nucleobases in length, which is the product of cleavage of a pre-microRNA by the enzyme Dicer. Examples of mature microRNAs are found in the microRNA database known as miRBase (http://microma.sanger.ac.uk/). In certain embodiments, microRNA is abbreviated as "microRNA" or "miR."

"microRNA-regulated transcript" means a transcript that is regulated by a microRNA.

"Seed sequence" means a nucleobase sequence comprising nucleobases 2 to 7 of the 5'-end of a mature microRNA sequence.

"Seed match sequence" means a nucleobase sequence that is complementary to a seed sequence, and is the same length as the seed sequence.

"Naturally occurring internucleoside linkage" means a 3' to 5' phosphodiester linkage between nucleosides.

"Natural sugar" means a sugar found in DNA (2'-H) or RNA (2'-OH).

"Internucleoside linkage" means a covalent linkage between adjacent nucleosides.

"Linked nucleosides" means nucleosides joined by a covalent linkage.

"Nucleobase" means a heterocyclic moiety capable of non-covalently pairing with another nucleobase.

"Nucleoside" means a nucleobase linked to a sugar moiety.

"Nucleotide" means a nucleoside having a phosphate group covalently linked to the sugar portion of a nucleoside.

"Compound comprising a modified oligonucleotide consisting of" a number of linked nucleosides means a compound that includes a modified oligonucleotide having the specified number of linked nucleosides. Thus, the compound may include additional substituents or conjugates. Unless otherwise indicated, the compound does not include any additional nucleosides beyond those of the modified oligonucleotide.

"Modified nucleoside" means a nucleoside having any change from a naturally occurring nucleoside. A modified nucleoside may have a modified sugar, and an unmodified nucleobase. A modified nucleoside may have a modified sugar and a modified nucleobase. A modified nucleoside may have a natural sugar and a modified nucleobase. In certain embodiments, a modified nucleoside is a bicyclic nucleoside. In certain embodiments, a modified nucleoside is a non-bicyclic nucleoside.

"2'-modified nucleoside" means a nucleoside comprising a sugar with any modification at the position equivalent to the 2' position of the furanosyl ring as the positions are numbered in 2-deoxyribose or ribose. It is to be understood that 2'-modified nucleosides include, without limitation, nucleosides comprising bicyclic sugar moieties.

"Modified internucleoside linkage" means any change from a naturally occurring internucleoside linkage.

"Phosphorothioate internucleoside linkage" means a linkage between nucleosides where one of the non-bridging atoms is a sulfur atom, i.e. OP(O)(S)O—. For the avoidance of doubt, the sulfur atom may be protonated or associated with a counterion, such as $Na^+$, $K^+$, etc.

"Phosphodiester linkage" means a linkage between nucleosides having the structure —OP(O)$_2$O—. For the avoidance of doubt, one of the non-bridging oxygens may be protonated or associated with a counterion, such as $Na^+$, $K^+$, etc.

"Unmodified nucleobase" means the naturally occurring heterocyclic bases of RNA or DNA: the purine bases adenine (A) and guanine (G), and the pyrimidine bases thymine (T), cytosine (C) (including 5-methylcytosine), and uracil (U).

"5-methylcytosine" means a cytosine comprising a methyl group attached to the 5 position of the cytosine ring.

"Non-methylated cytosine" means a cytosine that does not have a methyl group attached to the 5 position of the cytosine ring.

"Modified nucleobase" means any nucleobase that is not an unmodified nucleobase.

"Sugar moiety" means a naturally occurring furanosyl or a modified sugar moiety.

"Modified sugar moiety" means a substituted sugar moiety or a sugar surrogate.

"2'-O-methyl sugar" or "2'-OMe sugar" means a sugar having a O-methyl modification at the 2' position.

"2'-O-methoxyethyl sugar" or "2'-MOE sugar" means a sugar having a O-methoxyethyl modification at the 2' position.

"2'-O-fluoro" or "2'-F" means a sugar having a fluoro modification of the 2' position.

"Bicyclic sugar moiety" means a modified sugar moiety comprising a 4 to 7 membered ring (including by not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl. Nonlimiting exemplary bicyclic sugar moieties include LNA, ENA, cEt, S-cEt, and R-cEt.

"Locked nucleic acid (LNA) sugar moiety" means a substituted sugar moiety comprising a $(CH_2)$—O bridge between the 4' and 2' furanose ring atoms.

"ENA sugar moiety" means a substituted sugar moiety comprising a $(CH_2)_2$—O bridge between the 4' and 2' furanose ring atoms.

"Constrained ethyl (cEt) sugar moiety" means a substituted sugar moiety comprising a $CH(CH_3)$—O bridge between the 4' and the 2' furanose ring atoms. In certain embodiments, the $CH(CH_3)$—O bridge is constrained in the S orientation. In certain embodiments, the $CH(CH_3)$—O bridge is constrained in the R orientation.

"S-cEt sugar moiety" means a substituted sugar moiety comprising an S-constrained $CH(CH_3)$—O bridge between the 4' and the 2' furanose ring atoms.

"R-cEt sugar moiety" means a substituted sugar moiety comprising an R-constrained $CH(CH_3)$—O bridge between the 4' and the 2' furanose ring atoms.

"2'-O-methyl nucleoside" means a modified nucleoside having a 2'-O-methyl sugar modification.

"2'-O-methoxyethyl nucleoside" means a modified nucleoside having a 2'-O-methoxyethyl sugar modification. A 2'-O-methoxyethyl nucleoside may comprise a modified or unmodified nucleobase.

"2'-fluoro nucleoside" means a modified nucleoside having a 2'-fluoro sugar modification. A 2'-fluoro nucleoside may comprise a modified or unmodified nucleobase.

"Bicyclic nucleoside" means a modified nucleoside having a bicyclic sugar moiety. A bicyclic nucleoside may have a modified or unmodified nucleobase.

"cEt nucleoside" means a nucleoside comprising a cEt sugar moiety. A cEt nucleoside may comprise a modified or unmodified nucleobase.

"S-cEt nucleoside" means a nucleoside comprising an S-cEt sugar moiety.

"R-cEt nucleoside" means a nucleoside comprising an R-cEt sugar moiety.

"β-D-deoxyribonucleoside" means a naturally occurring DNA nucleoside.

"β-D-ribonucleoside" means a naturally occurring RNA nucleoside.

"LNA nucleoside" means a nucleoside comprising a LNA sugar moiety.

"ENA nucleoside" means a nucleoside comprising an ENA sugar moiety.

A "linking group" as used herein refers to an atom or group of atoms that attach a first chemical entity to a second chemical entity via one or more covalent bonds.

A "linker" as used herein, refers to an atom or group of atoms that attach one or more ligands to a modified or unmodified nucleoside via one or more covalent bonds. The modified or unmodified nucleoside may be part of a modified oligonucleotide as described herein, or may be attached to a modified oligonucleotide through a phosphodiester or phosphorothioate bond. In some embodiments, the linker attaches one or more ligands to the 3' end of a modified oligonucleotide. In some embodiments, the linker attaches one or more ligands to the 5' end of a modified oligonucleotide. In some embodiments, the linker attaches one or more ligands to a modified or unmodified nucleoside that is attached to the 3' end of a modified oligonucleotide. In some embodiments, the linker attaches one or more ligands to a modified or unmodified nucleoside that is attached to the 5' end of a modified oligonucleotide. When the linker attaches one or more ligands to the 3' end of a modified oligonucleotide or to a modified or unmodified nucleoside attached to the 3' end of a modified oligonucleotide, in some embodiments, the attachment point for the linker may be the 3' carbon of a modified or unmodified sugar moiety. When the linker attaches one or more ligands to the 5' end of a modified oligonucleotide or to a modified or unmodified nucleoside attached to the 5' end of a modified oligonucleotide, in some embodiments, the attachment point for the linker may be the 5' carbon of a modified or unmodified sugar moiety.

Overview

RG-101 is a GalNAc-conjugated modified oligonucleotide targeted to miR-122. In a completed Phase I human proof-of-concept study, treatment with a single subcutaneous dose of RG-101 as monotherapy resulted in significant viral load reductions in all treated HCV-infected subjects, including subjects with difficult to treat genotypes, various liver fibrosis status and those who have experienced viral relapse after a prior IFN-containing regimen.

In a completed Phase II study evaluating the combination of RG-101 with multiple approved direct-acting antiviral (DAA) drugs, all subjects receving RG-101 and Harvoni® experienced a significant and sustained viral load reduction throughout the 48-week follow up period. Response rates were less than 100% in groups receving RG-101 and Daklinza™ or Olysio@. During the Phase 2 study, 10 of 200 subjects experienced transient hyperbilirubinemia, characterized by increased conjugated and total bilirubin above the upper limit of normal (ULN). The U.S. Food and Drug Administration placed the IND for RG-101 for the treatment of chronic HCV infection on clinical hold.

While additional subject-specific contributing factors cannot be definitively excluded, as described herein it is believed that inhibition of conjugated bilirubin transport by RG-101 likely contributed to the observed hyperbilirubinemia. In view of this, a screen was conducted for alternative compounds targeting miR-122 that maintain potent HCV antiviral activity and have a suitable safety profile, including lack of substantial interference with bilirubin transport via the MRP2 transporter. This screening process identified compound RG6650 as an anti-miR-122 compound meeting these criteria.

Certain Anti-miR-122 Compounds

Provided herein is a compound named RG6650 comprising a GalNAc-containing conjugate moiety and a modified oligonucleotide complementary to miR-122. The modified oligonucleotide is named RG7443 and has the structure UsCsACsACsTCsCs, where nucleosides not followed by a subscript are β-D-deoxyribonucleosides, nucleosides followed by a subscript "S" are S-cEt nucleosides, and each internucleoside linkage is a phosphorothioate internucleoside linkage.

In certain embodiments, the compound RG6650 is represented by the structure:

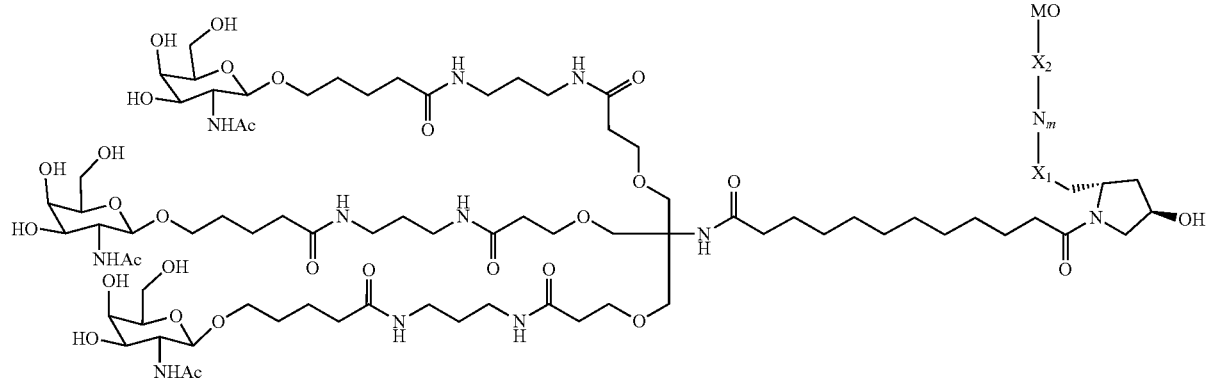

wherein the MO is a modified oligonucleotide and has the structure UsCsACsACsTCsCs, where nucleosides not followed by a subscript are β-D-deoxyribonucleosides, nucleosides followed by a subscript "S" are S-cEt nucleosides, and each internucleoside linkage is a phosphorothioate internucleoside linkage; wherein $X_1$ is a phosphodiester linkage; m is 1; N is a O-D-deoxyriboadenosine; $X_2$ is a phosphodiester linkage; and wherein the conjugate moiety is linked to the 3' terminus of the modified oligonucleotide.

In certain embodiments, the compound RG6650 is represented by the structure:

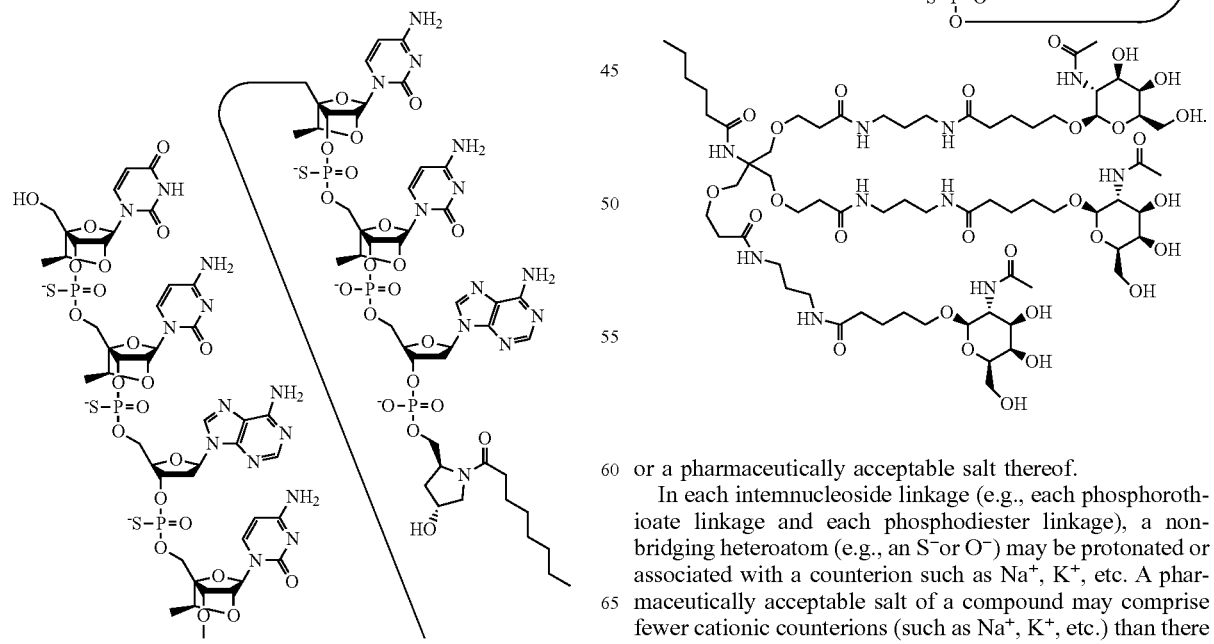

or a pharmaceutically acceptable salt thereof.

In each internucleoside linkage (e.g., each phosphorothioate linkage and each phosphodiester linkage), a non-bridging heteroatom (e.g., an $S^-$ or $O^-$) may be protonated or associated with a counterion such as $Na^+$, $K^+$, etc. A pharmaceutically acceptable salt of a compound may comprise fewer cationic counterions (such as $Na^+$, $K^+$, etc.) than there are phosphorothioate and/or phosphodiester linkages per molecule (i.e., some phosphorothioate and/or phosphodiester linkages are protonated and some are associated with counterions). In some embodiments, a pharmaceutically acceptable salt of RG6650 comprises fewer than 10 cationic counterions (such as $Na^+$, $K^+$, etc.) per molecule of RG6650. That is, in some embodiments, a pharmaceutically acceptable salt of RG6650 may comprise, on average, 1, 2, 3, 4, 5, 6, 7, 8 or 9 cationic counterions per molecule of RG6650, with the remaining phosphorothioate and/or phosphodiester linkages being protonated.

Provided herein are pharmaceutical compositions comprising a compound provided herein, and a pharmaceutically acceptable diluent. In certain embodiments, the pharmaceutically acceptable diluent is an aqueous solution. In certain embodiments, the aqueous solution is a saline solution. As used herein, pharmaceutically acceptable diluents are understood to be sterile diluents.

In certain embodiments, a pharmaceutical composition provided herein is administered by subcutaneous injection. Additional suitable administration routes include, without limitation, intravenous administration, oral administration, and intramuscular administration.

Certain Uses of Anti-miR-122 Compounds and Compositions

Provided here are methods for the treatment of HCV infection, comprising administering at least one dose of a compound or pharmaceutical composition provided herein to an HCV-infected subject. In certain embodiments, the methods provided herein comprise selecting an HCV-infected subject.

Although current direct-acting antivirals are achieving high rates of sustained viral response, there is an underserved population of HCV-infected subjects who do not respond to current treatments, or who relapse following successful treatment. Resistance to antiviral therapy is a major problem associated with a high mutation rate of HCV and is seen even with combinations of drugs. Additionally, poor HCV-infected subject compliance with treatment regimens requiring at least once daily adminstration of oral agents for extended periods (e.g. 12 weeks for Harvoni®) may interfere with achieving a high response rate. A treatment combining an anti-miR-122 therapeutic that targets the viral host factor miR-122, and one or more direct-acting antiviral agents, represents an opportunity to achieve higher and more durable cure rates, for example through improved subject compliance, reduced side effects, and/or greater efficacy. Accordingly, in certain embodiments, provided herein are methods comprising the concomitant administration of a compound or pharmaceutical composition provided herein and at least one direct-acting antiviral agent (DAA) during a treatment period.

In certain embodiments, the treatment period is substantially shorter than the treatment period for the at least one DAA alone.

Provided herein are methods of treating hepatitis C virus (HCV) infection comprising administering a compound or pharmaceutical composition provided herein and at least one direct-acting antiviral (DAA) to an HCVinfected subject during a treatment period, wherein the duration of the treatment period is 12 weeks or less, and wherein a start dose of the compound or pharmaceutical composition is administered at the start of the treatment period and an end dose of the compound or pharmaceutical composition is administered at the end of the treatment period. In certain embodiments, the start dose and the end dose are the only doses of the compound or pharmaceutical composition that are administered during the treatment period.

Provided herein are methods of treating HCV infection comprising administering a compound or pharmaceutical composition provided herein and at least one DAA to an HCV-infected subject during a treatment period, wherein the duration of the treatment period is 12 weeks or less, and wherein a start dose of the compound or pharmaceutical composition is administered at the start of the treatment period, and the start dose is the only dose of the compound or pharmaceutical composition that is administered during the treatment period.

Provided herein are methods of treating HCV infection comprising administering a compound or pharmaceutical composition provided herein and at least one DAA to an HCV-infected subject during a treatment period, wherein the duration of the treatment period is 12 weeks or less, and wherein an end dose of the compound or pharmaceutical composition is administered at the end of the treatment period, and the end dose is the only dose of the compound or pharmaceutical composition that is administered during the treatment period.

In any of the methods provided herein the duration of the treatment period is 11 weeks or less, 10 weeks or less, 9 weeks or less, 8 weeks or less, 7 weeks or less, 6 weeks or less, 5 weeks or less, 4 weeks or less, 2 weeks or less, or 1 week or less. In any of the methods provided herein, the duration of the treatment period is 1 to 12 weeks, 2 to 10 weeks, 4 to 8 weeks, 2 to 6 weeks, or 1 to 4 weeks. In any of the methods provided herein, the duration of the treatment period is 11 weeks, 10 weeks, 9 weeks, 8 weeks, 7 weeks, 6 weeks, or 5 weeks. In certain embodiments, the duration of the treatment period is 11 weeks. In certain embodiments, the duration of the treatment period is 10 weeks. In certain embodiments, the duration of the treatment period is 9 weeks. In certain embodiments, the duration of the treatment period is 8 weeks. In certain embodiments, the duration of the treatment period is 7 weeks. In certain embodiments, the duration of the treatment period is 6 weeks. In certain embodiments, the duration of the treatment period is 5 weeks.

In certain embodiments, the duration of the treatment period is 4 weeks. In certain embodiments, the duration of the treatment period is 3 weeks. In certain embodiments, the duration of the treatment period is 2 weeks. In certain embodiments, the duration of the treatment period is 1 week. In certain embodiments, the duration of the treatment period is 26, 27, 28, 29, or 30 days. In certain embodiments, the duration of the treatment period is 28 or 29 days. In certain embodiments, the duration of the treatment period is 18, 19, 20, 21, or 22 days. In certain embodiments, the duration of the treatment period is 21 days. In certain embodiments, the duration of the treatment period is 12, 13, 14, 15, or 16 days. In certain embodiments, the duration of the treatment period is 14 or 15 days. In certain embodiments, the duration of the treatment period is 6, 7, or 8 days. In certain embodiments, the duration of the treatment period is 7 or 8 days.

In certain embodiments, the start dose of the compound or pharmaceutical composition and the first dose of the at least one DAA are administered within seven days of each other. In certain embodiments, the start dose of the compound or pharmaceutical composition is administered one day before the first dose of the at least one DAA. In certain embodiments, the start dose of the compound or pharmaceutical composition is administered on the same day as the first dose of the at least one DAA. In certain embodiments, the start dose of the compound or pharmaceutical composition is administered one day after the first dose of the at least one DAA. In certain embodiments, the end dose of the compound or pharmaceutical composition and the last dose of the at least one DAA are administered within 7 days of each other. In certain embodiments, the end dose of the compound or pharmaceutical composition is administered one day prior to the last dose of the at least one DAA. In certain embodiments, the end dose of the compound or pharmaceutical composition is administered on the same day as the last dose of the at least one DAA. In certain embodiments, the end dose of the compound or pharmaceutical composition is administered on the day after the last dose of the at least one DAA.

In certain embodiments, a compound provided herein is administered at a dose of 5 mg/kg or less, 4.5 mg/kg or less, 4 mg/kg or less, 3.5 mg/kg or less, 3 mg/kg or less, 2.5 mg/kg or less, 2 mg/kg or les, 1.5 mg/kg or less, 1 mg/kg or less, 0.75 mg/kg or less, 0.5 mg/kg or less, or 0.25 mg/kg or less.

In certain embodiments, the HCV-infected subject is infected with genotype 1. In certain embodiments, the HCV-infected subject is infected with genotype 1a. In certain embodiments, the HCV-infected subject is infected with genotype 1b. In certain embodiments, the HCV-infected subject is infected with genotype 2. In certain embodiments, the HCV-infected subject is infected with genotype 3. In certain embodiments, the HCV-infected subject is infected with genotype 4. In certain embodiments, the HCV-infected subject is infected with genotype 5. In certain embodiments, the HCV-infected subject is infected with genotype 6.

In certain embodiments, the HCV-infected subject is infected with genotype 1a, genotype 1b, genotype 2a, genotype 2b, genotype 2c, genotype 2d, genotype 3a, genotype 3b, genotype 3c, genotype 3d, genotype 3e, genotype 3f, genotype 4a, genotype 4b, genotype 4c, genotype 4d, genotype 4e, genotype 4f, genotype 4g, genotype 4h, genotype 4i, genotype 4j, genotype 5a, or genotype 6a.

The HCV genome encodes several proteins essential for viral RNA replication and virion assembly. The HCV genome is capable of mutating at a high rate. In some instances, treatment with a DAA results in the emergence of a nucleotide sequence polymorphism, which may be associated with resistance of the virus to the DAA. Accordingly, provided herein are methods of treatment of HCV-infected subjects infected with an HCV genotype having one or more resistance-associated polymorphisms. In certain embodiments, the HCV-infected subject is tested for the presence of one or more resistance-associated polymorphisms prior to treatment. The presence of a polymorphism may be determined, in some embodiments, by sequencing the HCV RNA.

In certain embodiments, present in the HCV RNA are nucleotide changes that encode one or more amino acid polymorphisms in one or more HCV-encoded proteins. In certain embodiments, the amino acid polymorphism is in the HCV-encoded NS5A protein. In certain embodiments, an NS5A amino acid polymorphism is at one or more of amino acid positions M28, Q30, L31, and Y93 of the NS5A protein. In certain embodiments, the amino acid polymorphism is in the HCV-encoded NS3 protein. In certain embodiments, the amino acid polymorphism is at one or more of positions Q80, S122, R155, D168, and D169 of the NS3 protein. In certain embodiments, the amino acid polymorphism is in the HCV-encoded NS4A protein. In certain embodiments, the amino acid polymorphism is in the HCV-encoded NS4B protein. In certain embodiments, the amino acid polymorphism is in the HCV-encoded NS5B protein.

In certain embodiments, the HCV-infected subject is a treatment-naïve HCV-infected subject, i.e. the subject has not received treatment prior to being selected for treatment as provided herein. In certain embodiments, the treatment does not include administration of interferon to the HCV-infected subject. In certain embodiments, the HCV-infected subject is an interferon non-responder. In certain embodiments, an HCV-infected subject is a direct-acting anti-viral non-responder.

HCV-infected subjects may develop HCV-associated diseases. The major hematological consequence of HCV infection is cirrhosis and complications thereof including hemorrhage, hepatic insufficiency, and hepatocellular carcinoma. An additional complication is fibrosis, which is the result of chronic inflammation causing the deposition of extracellular matrix component, which leads to distortion of the hepatic architecture and blockage of the microcirculation and liver function. A further complication of HCV infection is steatosis, which may in turn lead to extrahepatic pathologies including diabetes, protein malnutrition, hypertension, cell toxins, obesity, and anoxia. As complications increase in severity, the liver may eventually fail and the HCV-infected subject may require liver transplantation. HCV-infected subjects may also develop hepatocellular carcinoma. In certain embodiments, an HCV-infected subject has an HCV-associated disease. In certain embodiments, the HCV-associated disease is cirrhosis, fibrosis, steatohepatitis, steatosis, and/or hepatocellular carcinoma.

In certain embodiments, the HCV-infected subject is a liver transplant recipient.

In certain embodiments, an HCV-infected subject is infected with one or more viruses other than HCV. In certain embodiments, the HCV-infected subject is and HCV/HIV co-infected subject, i.e. the subject is infected with both HCV and HIV. In certain embodiments, the methods provided herein comprise administration of an anti-viral agent used in the treatment of HIV infection. In certain embodiments, an additional therapeutic agent is a non-nucleoside reverse transcriptase inhibitors (NNRTIs). In certain embodiments, an additional therapeutic agent is a nucleoside reverse transcriptase inhibitors (NRTIs). In certain embodiments, an additional therapeutic agent is a protease inhibitor. In certain embodiments, an additional therapeutic agent is an entry inhibitor or fusion inhibitor. In certain embodiments, an additional therapeutic agent is an integrase inhibitor. In certain embodiments, an additional therapeutic agent is selected from efavirenz, etravirine, nevirapine, abacavir, emtricitabine, tenofovir, lamivudine, zidovudine, atazanavir, darunavir, fosamprenavir, ritonavir, enfuvirtide, maraviroc, and raltegravir.

In certain embodiments, the HCV-infected subject is an HCV-infected subject with renal impairment. Renal impairment may be evaluated by determining estimated glomerular filtration rate (eGFR). In certain embodiments, the subject has mild renal impairment. In certain embodiments, mild renal impairment is characterized by a glomerular filtration rate of 60-89 ml/min/1.73 $m^2$. In certain embodiments, the subject has moderate renal impairment. In certain embodiments, moderate renal impairment is characterized by a glomerular filtration rate of 30-59 ml/min/1.73 $m^2$. In certain embodiments, the subject has severe renal impairment. In certain embodiments, severe renal impairment is characterized by a glomerular filtration rate of 15-29 ml/min/1.73 $m^2$. In certain embodiments, the subject is experiencing kidney failure. In certain embodiments, a subject experiencing kidney failure has a glomerular filtration rate of less than 15 ml/min/1.73 $m^2$. The dosage of compound or DAA administered to an HCV-infected subject with renal impairment may be adjusted higher or lower than the dosage administered to a subject not having renal impairment, depending on the pharmacokinetic behavior of the drug in the subjects with renal impairment.

In certain embodiments, the treatment provided herein the symptoms of HCV infection. While HCV infection is often asymptomatic, when present, symptoms of HCV infection include, without limitation, pain within or around the liver, jaundice, nausea, loss of appetite, and fatigue.

HCV RNA level may be used to diagnose HCV infection, monitor disease activity and/or monitor an HCV-infected subject's response to treatment. In certain embodiments, a treatment provided herein reduces HCV RNA level. In certain embodiments, the methods provided herein comprise administering a compound or pharmaceutical composition and a DAA, in an amount effective to treat the HCV infection. In certain embodiments, the methods provided herein comprise selecting a subject having an HCV RNA level greater than 350,000 copies per milliliter of serum, between 350,000 and 3,500,000 copies per milliliter of serum, or greater than 3,500,000 copies per milliliter of serum. In certain embodiments, the methods provided herein comprise reducing HCV RNA level. In certain embodiments, the methods provided herein comprise reducing HCV RNA level to below 200 copies per milliliter of serum, to below 100 copies per milliliter of serum, to below 40 copies per milliliter of serum. HCV RNA level may be referred to as "viral load" or "HCV RNA titer."

Changes to HCV RNA level may be described as log changes. For example, a drop from 60,000 to 600 would be a 2-log drop in HCV RNA level. In certain embodiments, the methods provided herein achieve a HCV RNA level decrease greater than or equal to 2 logs. In certain embodiments, the methods provided herein achieve an HCV RNA level decrease of at least 0.5 fold, at least 1 fold, at least 1.5 fold, at least 2 fold, at least 10 fold, at least 50 fold, at least 100 fold, at least 500 fold, at least 1000 fold, at least 5000 fold, or at least 10,000 fold.

In certain embodiments, the methods provided herein comprise achieving a sustained virological response. In certain embodiments, the HCV RNA level is below a lower limit of quantitation (LLOQ) of prior to or at the end of the treatment period. In certain embodiments, HCV RNA level is below the LLOQ at 4 weeks after the end of the treatment period. In certain embodiments, the HCV RNA level is below the LLOQ at 8 weeks after the end of the treatment period. In certain embodiments, the HCV RNA level is below the LLOQ at 12 weeks after the end of the treatment period. In certain embodiments, the HCV RNA level is below the LLOQ at 24 weeks after the end of the treatment period. In certain embodiments, the HCV RNA level is below the LLOQ at 36 weeks after the end of the treatment period.

In certain embodiments, the HCV RNA level is below the LLOQ at 48 weeks after the end of the treatment period. In certain embodiments, the LLOQ is 25 IU/mL. In certain embodiments, the LLOQ is 15 IU/mL. In certain embodiments, the LLOQ is 12 IU/mL.

In certain embodiments, HCV RNA level is quantitated using a real-time polymerase chain reaction-based assay. Assays may differ in the lower limit of quantitation (LLOQ). For example, The COBAS TaqMan HCV test (version 2.0) for use with the High Pure System has a lower limit of quantification (LLOQ) of 25 IU per mL and the COBAS AmpliPrep/COBAS Taqman HCV test (version 2.0) has a LLOQ of 15 IU per mL. The lower limit of quantitation (LLOQ) for the Abbott RealTime HCV test is 12 IU per mL.

Following an HCV treatment regimen, an HCV-infected subject may experience a decrease in HCV RNA level, followed by an increase in HCV RNA level, which subsequent increase is known as a rebound in HCV RNA level. In certain embodiments, the methods provided herein prevent a rebound in HCV RNA level. In certain embodiments, the methods provided herein delay a rebound in HCV RNA level.

In any of the embodiments provided herein, the at least one DAA is administered once daily or twice daily. In certain embodiments, the at least one DAA is administered once daily. In certain embodiments, the at least one DAA is administered twice daily. In certain embodiments, the at least one DAA is selected from an NS3/4A protease inhibitor, an NS5A inhibitor, a nucleoside NS5B polymerase inhibitor, and a non-nucleoside NS5B polymerase inhibitor. In certain embodiments, an NS5A inhibitor is elbasvir. In certain embodiments, an NS3/4A protease inhibitor is grazoprevir. In certain embodiments, an NS5A inhibitor is ombitasvir. In certain embodiments, an NS3/4A protease inhibitor is paritaprevir. In certain embodiments, a non-nucleoside NS5B polymerase inhibitor is dasbuvir. In certain embodiments, an NS5A inhibitor is daclatasvir. In certain embodiments, an NS3/4A protease inhibitor is simeprevir. In certain embodiments, an NS5A inhibitor is ledipasvir. In certain embodiments, an NS5B polymerase inhibitor is sofosbuvir. In certain embodiments, an NS3/4A inhibitor is glecaprevir. In certain embodiments, an NS5A inhibitor is pibrentasvir. In certain embodiments, one or more direct-acting anti-viral agents is administered.

In certain embodiments, the at least one DAA is selected from sofosbuvir, ledipasvir, ombitasvir, dasabuvir, elbasvir, grazoprevir, ribavirin, ombitasvir, paritaprevir, ritonavir, boceprevir, vaniprevir, asunaprevir, daclatasvir, simeprevir, mericitabine, tegobuvir, danoprevir, sovaprevir, glecaprevir, pibrentasvir, voxilaprevir, velpatasvir, and GSK2878175. In certain embodiments, the at least one DAA is administered in an amount effective to treat the HCV infection. In certain embodiments, the at least one DAA is administered for a treatment period that is shorter than the treatment period prescribed when the DAA is administered without a compound or pharmaceutical composition provided herein.

In certain embodiments, the at least one DAA comprises sofosbuvir. In certain embodiments, the at least one DAA comprises 400 mg of sofosbuvir. In certain embodiments, the at least one DAA is one tablet comprising 400 mg sofosbuvir, administered orally once daily. Sofosbuvir may be administered with or without ribavirin.

In certain embodiments, the at least one DAA comprises ledipasvir and sofosbuvir. In certain embodiments, the at least one DAA comprises ledipasvir administered at a dose of 90 mg of ledipasvir and sofosbuvir at a dose of 400 mg. In certain embodiments, the at least one DAA is one tablet comprising 90 mg of ledipasvir and 400 mg sofosbuvir, administered orally once daily.

In certain embodiments, the at least one DAA comprises simeprevir or a salt form thereof. In certain embodiments, the at least one DAA comprises simeprevir administered at a dosage of 150 mg. In certain embodiments, the at least one DAA is one capsule comprising 150 mg of simeprevir, administered orally once daily.

In certain embodiments, the at least one DAA comprises daclatasvir or a salt form thereof. In certain embodiments, the at least one DAA comprises daclatasvir administered at a dosage of 60 mg. In certain embodiments, the at least one DAA is one tablet comprising 60 mg of daclatasivir, administered orally once daily. In certain embodiments, the at least one DAA is two tablets each comprising 30 mg of daclatasvir, administered orally once daily. In certain embodiments, the at least one DAA comprises daclatasivr administered at a dose of 60 mg and sofosbuvir administered at a dose of 400 mg. In certain embodiments, the HCV-infected subject is determined to be infected with an HCV genotype having one or more resistance-associated polymorphisms. In certain embodiments, the resistance-associated polymorphism is an NS5A polymorphism. In certain embodiments, the NS5A polymorphism is at one or more of positions M28, Q30, L31, and Y93.

In certain embodiments, the at least one DAA comprises glecaprevir and pibrentasvir, or salt forms thereof. In certain embodiments, the at least one DAA comprises glecapravir administered at a dosage of 100 mg and pibrentasvir administered at a dosage of 40 mg. In certain embodiments, the at least one DAA is three tablets each containing 100 mg glecapravir and 40 mg pibrentasvir, administered orally one daily.

In certain embodiments, the at least one DAA comprises ombitasvir, paritaprevir, ritonavir, and dasabuvir, or salt forms thereof. In certain embodiments, the at least one DAA comprises ombitasvir administered at a dosage of 12.5 mg, paritaprevir administered at a dosage of 75 mg, ritonavir administered at a dosage of 50 mg, and dasabuvir administered at a dosage of 250 mg. In certain embodiments, the at least one DAA is two tablets each containing 12.5 mg ombitasvir, 75 mg paritaprevir, 50 mg ritonavir, administered orally once daily, and one tablet comprising 250 mg of dasabuvir, administered twice daily.

In certain embodiments, the at least one DAA comprises ombitasvir, paritaprevir, ritonavir, dasabuvir, and ribavirin. In certain embodiments, the at least one DAA comprises ombitasvir administered at a dosage of 12.5 mg, paritaprevir administered at a dosage of 75 mg, ritonavir administered at a dosage of 50 mg, and ribavirin administered at a dose of 800 mg, 1000 mg 1200 mg, or 1400 mg. In certain embodiments, the at least one DAA is two tablets each containing 12.5 mg ombitasvir, 75 mg paritaprevir, 50 mg ritonavir, administered orally once daily, one tablet comprising 250 mg of dasabuvir, administered twice daily, and ribavirin administered at a dose of 800 mg, 1000 mg, 1200 mg, or 1400 mg.

In certain embodiments, the at least one DAA comprises elbasvir and grazoprevir. In certain embodiments, the at least one DAA comprises elbasvir administered at a dose of 50 mg and grazoprevir administered at a dose of 100 mg. In certain embodiments, the at least one DAA is one tablet comprising 50 mg elbasvir and 100 mg grazoprevir, administered orally once daily.

In certain embodiments, the at least one DAA comprises elbasvir, grazoprevir and ribavirin. In certain embodiments, the at least one DAA comprises elbasvir administered at a dose of 50 mg, grazoprevir administered at a dose of 100 mg and ribavirin administered at a dose of 800 mg, 1000 mg, 1200 mg, or 1400 mg. In certain embodiments, the at least one DAA is one tablet comprising 50 mg elbasvir and 100 mg grazoprevir, administered orally once daily, and ribavirin administered at a dose of 1000 mg, 1200 mg, or 1400 mg. In certain embodiments, the HCV-infected subject is determined to be infected with an HCV genotype having one or more resistance-associated polymorphisms. In certain embodiments, the resistance-associated polymorphism is an NS5A polymorphism. In certain embodiments, the NS5A polymorphism is at one or more of positions M28, Q30, L31, and Y93.

The recommended dosage of ribavirin is weight-based. In certain embodiments, the daily dosage of ribavirin is 1000 mg for subjects weighing less than 75 kg. In certain embodiments, the daily dosage is 1200 mg of ribavirin for subjects weighing 75 or more kg.

In certain embodiments, the daily dosage is administered orally in two divided doses, one dose in the morning and one dose in the evening. In certain embodiments, ribavirin is provided as a capsule comprising 200 mg ribavirin.

In certain embodiments, the daily dosage of ribavirin is 800 mg for subjects weighing less than 66 kg. In certain embodiments, the daily dosage of ribavirin is 1000 mg for subjects weighing 66 to 80 kg. In certain embodiments, the daily dosage of ribavirin is 1200 mg for subjects weighing 81 to 105 kg. In certain embodiments, the daily dosage of ribavirin is 1400 mg for subjects weighing more than 105 kg.

The administration of a compound or pharmaceutical composition provided herein may allow for the reduction of the dose amount or frequency of an at least one DAA administered to an HCV-infected subject. Reducing the amount or frequency of one or more DAAs administered may reduce side effects and/or improve subject compliance. Accordingly, in certain embodiments, the dose of the at least one DAA administered during the treatment period is a lower dose than when the DAA is administered alone.

For example, the at least one DAA may be administered at a dose that is 25% lower than when the at least one DAA is administered alone. In certain embodiments, the dose of the at least one DAA administered during the treatment period is administered less frequently than when the at least one DAA is administered alone. For example, the least one DAA may be administered once weekly, rather than once daily. In certain embodiments, both the amount and frequency of the at least one DAA administered are lower than when the at least one DAA is administered alone.

In certain embodiments, a compound provided herein and the at least one DAA are administered as a single pharmaceutical composition, i.e. the compound and at least one DAA are co-formulated in a pharmaceutical composition. Suitable administration routes include subcutaneous, intravenous, oral, or intramuscular administration.

In certain embodiments, one or more additional therapeutic agents is administered to the HCV-infected subject. In certain embodiments, the one or more additional therapeutic agents comprises an immune therapy, an immunomodulator, therapeutic vaccine, antifibrotic agent, anti-inflammatory agent, bronchodilator, mucolytic agent, anti-muscarinic, anti-leukotriene, inhibitor of cell adhesion, anti-oxidant, cytokine agonist, cytokine antagonist, lung surfactant, antimicrobial, an anti-cancer agent, an RNAi agent or a cyclophilin inhibitor.

In certain embodiments, the one or more additional therapeutic agents may be selected from a cofactor inhibitor, an HCV structural protein inhibitor, a cyclophilin inhibitor, an entry inhibitor, a TLR7 agonist, and an interferon.

While the goal of most current therapies is to eliminate the use of interferon, in some HCV-infected subjects, treatment with interferon may be warranted. In certain embodiments, the additional therapeutic agent is selected from an interferon, ribavirin, and telaprevir. In certain embodiments, the interferon is selected from interferon alfa-2a, interferon alpha-2b, interferon alfacon-1, peginterferon alpha-2b, and peginterferon alpha-2a.

An HCV-infected subject may experience abnormal liver function, which is assessed by measuring one or more of bilirubin, albumin, and prothrombin time. Measurement of the liver enzymes alanine aminotransferase (ALT), and aspartate aminotransferase (AST) is performed to assess liver inflammation. One or more abnormal levels of these markers may indicate abnormal liver function. In certain embodiments, the methods provided herein comprise normalizing liver function. In certain embodiments, the methods provided herein comprise normalizing liver enzyme levels.

In any of the methods provided herein, the compound may be present in a pharmaceutical composition.

The compounds provided herein may be for use in therapy. In certain embodiments, the compound is for use in treating an HCV-infected subject. The compound for use in treating an HCV-infected subject may, in certain embodiments, be for use in any method of treatment described herein.

Administration of an anti-miR-122 compound to an HCV-infected subject results in reduced serum cholesterol, and as such may be used as a biomarker to assess the activity of an anti-miR-122 compound provided herein, alone or in addition to another indicator of efficacy, e.g. reduction in HCV RNA levels. Accordingly, provided herein are methods comprising administering a compound or pharmaceutical composition provided herein to an HCV-infected subject, collecting a blood sample from the subject, and measuring cholesterol in the blood sample from the HCV-infected subject. The level of cholesterol may be used as an indicator of anti-miR-122 compound activity in the HCV-infected subject.

Certain Modifications

In certain embodiments, provided herein are compounds wherein features of the conjugate moiety, for example a linker or a ligand, are modified in a manner that retains the desired properties of the compound, e.g. potency in reducing HCV RNA levels in an HCV-infected subject, and lack of significant inhibition of the MRP2 transporter.

RG6650 and compounds comprising RG7443 may be described by Structure C:

$L_n$-linker-$X_1$—$N_m$-$X_2$MO;

wherein each L is, independently, a ligand and n is from 1 to 10; each N is, independently, a modified or unmodified nucleoside and m is from 1 to 5; $X_1$ is a phosphodiester linkage or a phosphorothioate linkage; $X_2$ is a phosphodiester linkage or a phosphorothioate linkage; and MO is RG7443.

For example, RG6650 may be described by the following embodiment of Structure C:

wherein the MO is a modified oligonucleotide and has the structure UsCsACsACsTCsCs (RG7443), where nucleosides not followed by a subscript are β-D-deoxyribonucleosides, nucleosides followed by a subscript "S" are S-cEt nucleosides, and each internucleoside linkage is a phosphorothioate internucleoside linkage; wherein $X_1$ is a phosphodiester linkage; m is 1; N is a j-D-deoxyriboadenosine; $X_2$ is a phosphodiester linkage; and wherein the conjugate moiety is linked to the 3' terminus of the modified oligonucleotide.

In certain embodiments, one or more ligands of Structure C may be a ligand that, like the GalNAc moiety, facilitates uptake in the liver. Such ligands include cholesterol, and other ligands having affinity for the asialoglycoprotein receptor (ASGPR), including but not limited to galactose or a galactose derivative. In certain embodiments, a ligand having affinity for the ASGPR is N-acetylgalactosamine, galactose, galactosamine, N-formylgalactosamine, N-propionyl-galactosamine, N-n-butanoylgalactosamine, or N-iso-butanoyl-galactosamine.

In certain embodiments, when n is greater than 1, the linker comprises a scaffold capable of linking more than one L to the remainder of the compound (i.e., to the modified oligonucleotide (MO), to $X_1$—$N_m$—$X_2$-MO, to X—$N_m$—Y-MO, etc.). In some such embodiments, the La-linker portion of the compound (such as a compound of Structure A, B, C, or D) comprises Structure E:

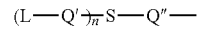

wherein each L is, independently, a ligand; n is from 1 to 10; S is a scaffold; and Q' and Q" are, independently, linking groups.

In certain embodiments, each Q' and Q" is independently selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid.

In certain embodiments, a scaffold links 2, 3, 4, or 5 ligands to a modified oligonucleotide. In certain embodiments, a scaffold links 3 ligands to a modified oligonucleotide.

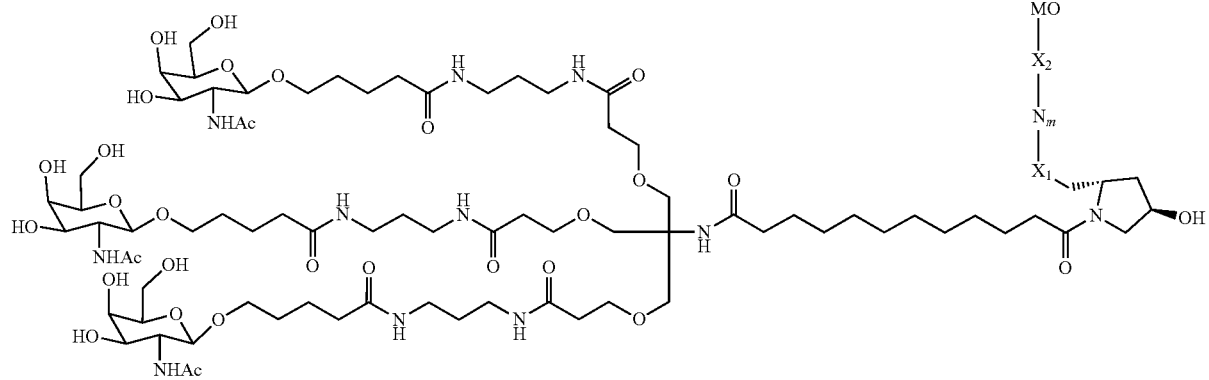

A nonlimiting exemplary Structure E is Structure E(i):

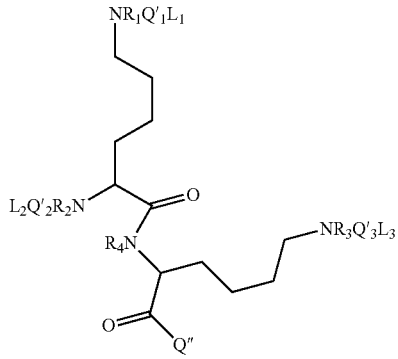

wherein $L_1$, $L_2$, and $L_3$ are each, independently, a ligand; $Q'_1$, $Q'_2$, $Q'_3$, and $Q''$ are each, independently, a linking group; and $R_1$, $R_2$, $R_3$, and $R_4$ are each, independently, selected from H, $C_1$-$C_6$ alkyl, and substituted $C_1$-$C_6$ alkyl.

In some embodiments, $Q'_1$, $Q'_2$, $Q'_3$, and $Q''$ are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, $R_3$, and $R_4$ are each, independently, selected from H, methyl, ethyl, propyl, isopropyl, and butyl. In some embodiments, $R_1$, $R_2$, $R_3$, and $R_4$ are each selected from H and methyl.

A further nonlimiting exemplary Structure E is Structure E(ii):

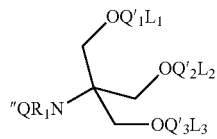

wherein $L_1$, $L_2$, and $L_3$ are each, independently, a ligand; $Q'_1$, $Q'_2$, $Q'_3$, and $Q''$ are each, independently, a linking group; and $R_1$ is selected from H, $C_1$-$C_6$ alkyl, and substituted $C_1$-$C_6$ alkyl.

In some embodiments, $Q'_1$, $Q'_2$, $Q'_3$, and $Q''$ are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$ is selected from H, methyl, ethyl, propyl, isopropyl, and butyl. In some embodiments, $R_1$ is H or methyl.

A further nonlimiting exemplary Structure E is Structure E(iii):

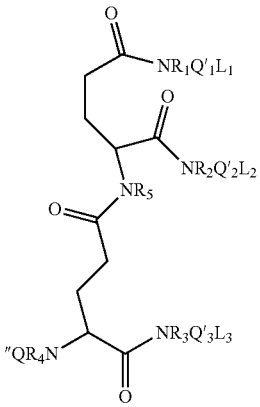

wherein $L_1$, $L_2$, and $L_3$ are each, independently, a ligand; $Q'_1$, $Q'_2$, $Q'_3$, and $Q''$ are each, independently, a linking group; and $R_1$, $R_2$, $R_3$, $R_4$, and $R_5$ are each, independently, selected from H, $C_1$-$C_6$ alkyl, and substituted $C_1$-$C_6$ alkyl.

In some embodiments, $Q'_1$, $Q'_2$, $Q'_3$, and $Q''$ are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, $R_3$, $R_4$, and $R_5$ are each, independently, selected from H, methyl, ethyl, propyl, isopropyl, and butyl. In some embodiments $R_1$, $R_2$, $R_3$, $R_4$, and $R_5$ are each selected from H and methyl.

A further nonlimiting exemplary Structure E is Structure E(iv):

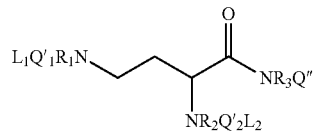

wherein $L_1$ and $L_2$ are each, independently, a ligand; $Q'_1$, $Q'_2$, and $Q''$ are each, independently, a linking group; and $R_1$, $R_2$, and $R_3$ are each, independently, selected from H, $C_1$-$C_6$ alkyl, and substituted $C_1$-$C_6$ alkyl.

In some embodiments, $Q'_1$, $Q'_2$, and $Q''$ are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, and $R_3$ are each, independently, selected from H, methyl, ethyl, propyl, isopropyl, and butyl. In some embodiments $R_1$, $R_2$, and $R_3$ are each selected from H and methyl.

A further nonlimiting exemplary Structure E is Structure E(v):

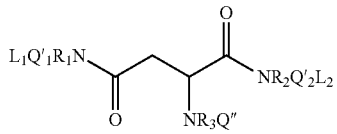

wherein $L_1$ and $L_2$ are each, independently, a ligand; $Q'_1$, $Q'_2$, and $Q''$ are each, independently, a linking group; and $R_1$, $R_2$, and $R_3$ are each, independently, selected from H, $C_1$-$C_6$ alkyl, and substituted $C_1$-$C_6$ alkyl.

In some embodiments, $Q'_1$, $Q'_2$, and $Q''$ are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, and $R_3$ are each, independently, selected from H, methyl, ethyl, propyl, isopropyl, and butyl. In some embodiments $R_1$, $R_2$, and $R_3$ are each selected from H and methyl.

A further nonlimiting exemplary Structure E is Structure E(vi):

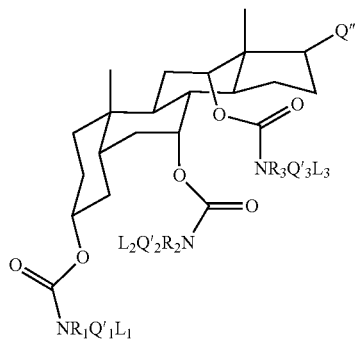

wherein $L_1$, $L_2$, and $L_3$ are each, independently, a ligand; $Q'_1$, $Q'_2$, $Q'_3$, and $Q''$ are each, independently, a linking group; and $R_1$, $R_2$, and $R_3$ are each, independently, selected from H, $C_1$-$C_6$ alkyl, and substituted $C_1$-$C_6$ alkyl.

In some embodiments, $Q'_1$, $Q'_2$, $Q'_3$, and $Q''$ are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, and $R_3$ are each, independently, selected from H, methyl, ethyl, propyl, isopropyl, and butyl. In some embodiments $R_1$, $R_2$, and $R_3$ are each selected from H and methyl.

A further nonlimiting exemplary Structure E is Structure E(vii):

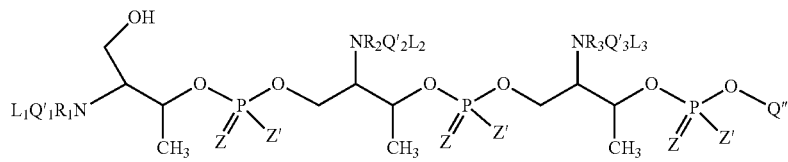

wherein $L_1$, $L_2$, and $L_3$ are each, independently, a ligand; $Q'_1$, $Q'_2$, $Q'_3$, and $Q''$ are each, independently, a linking group; $R_1$, $R_2$, and $R_3$ are each, independently, selected from H, $C_1$-$C_6$ alkyl, and substituted $C_1$-$C_6$ alkyl; and Z and Z' are each independently selected from O and S.

In some embodiments, $Q'_1$, $Q'_2$, $Q'_3$, and $Q''$ are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, and $R_3$ are each, independently, selected from H, methyl, ethyl, propyl, isopropyl, and butyl. In some embodiments $R_1$, $R_2$, and $R_3$ are each selected from H and methyl. In some embodiments, Z or Z' on at least one P atom is S, and the other Z or Z' is O (i.e., a phosphorothioate linkage). In some embodiments, each —OP(Z)(Z')O— is a phosphorothioate linkage. In some embodiments, Z and Z' are both O on at least one P atom (i.e., a phosphodiester linkage). In some embodiments, each —OP(Z)(Z')O— is a phosphodiester linkage.

A further nonlimiting exemplary Structure E is Structure E(viii):

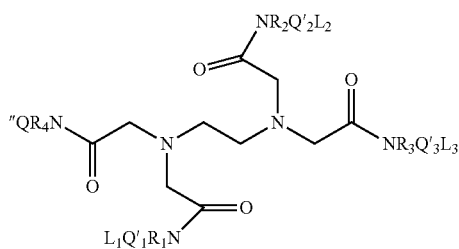

wherein $L_1$, $L_2$, and $L_3$ are each, independently, a ligand; $Q'_1$, $Q'_2$, $Q'_3$, and $Q''$ are each, independently, a linking group; and $R_1$, $R_2$, $R_3$, and $R_4$ are each, independently, selected from H, $C_1$-$C_6$ alkyl, and substituted $C_1$-$C_6$ alkyl.

In some embodiments, $Q'_1$, $Q'_2$, $Q'_3$, and $Q''$ are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, $R_3$, and $R_4$ are each, independently, selected from H, methyl, ethyl, propyl, isopropyl, and butyl. In some embodiments $R_1$, $R_2$, $R_3$, and $R_4$ are each selected from H and methyl.

Nonlimiting exemplary scaffolds and/or linkers comprising scaffolds, and synthesis thereof, are described, e.g., PCT Publication No. WO 2013/033230, U.S. Pat. No. 8,106,022 B2, U.S. Publication No. 2012/0157509 A1; U.S. Pat. Nos. 5,994,517, 7,491,805 B2; U.S. Pat. No. 8,313,772 B2; Manoharan, M., Chapter 16, Antisense Drug Technology, Crooke, S. T., Marcel Dekker, Inc., 2001, 391-469.

In certain embodiments, the $L_m$-linker portion of the compound comprises Structure F:

wherein:
B is selected from —O—, —S—, —N($R^N$)—, —Z—P(Z')(Z")O—, —Z—P(Z')(Z")O—$N_m$—X—, and —Z—P(Z')(Z")O—$N_m$—Y—;
MO is RG7443;
$R^N$ is selected from H, methyl, ethyl, propyl, isopropyl, butyl, and benzyl;
Z, $Z^+$, and Z" are each independently selected from O and S;
each N is, independently, a modified or unmodified nucleoside;
m is from 1 to 5;
X is selected from a phosphodiester linkage and a phosphorothioate linkage;
Y is a phosphodiester linkage; and the wavy line indicates the connection to the rest of the linker and ligand(s).

In certain embodiments, the wavy line indicates a connection to Structure E, above.

In certain embodiments, n is from 1 to 5, 1 to 4, 1 to 3, or 1 to 2. In certain embodiments, n is 1.

In certain embodiments, n is 2. In certain embodiments, n is 3. In certain embodiments, n is 4. In certain embodiments, n is 5.

In certain embodiments, the La-linker portion of the compound comprises Structure G:

wherein:
B is selected from —O—, —S—, —N($R^N$)—, —Z—P(Z')(Z")O—, —Z—P(Z')(Z")O—$N_m$—X—, and —Z—P(Z')(Z")O—$N_m$—Y—;
MO is RG7443;
$R^N$ is selected from H, methyl, ethyl, propyl, isopropyl, butyl, and benzyl;
Z, Z', and Z" are each independently selected from O and S;
each N is, independently, a modified or unmodified nucleoside;
m is from 1 to 5;
X is selected from a phosphodiester linkage and a phosphorothioate linkage;
Y is a phosphodiester linkage;
each L is, independently, a ligand; n is from 1 to 10; S is a scaffold; and Q' and Q" are, independently, linking groups.

In certain embodiments, each Q' and Q" are independently selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid.

A nonlimiting exemplary La-linker portion (e.g., of Structure F or G) of a compound is shown in Structure H below:

wherein the wavy line indicates attachment to the modified oligonucleotide RG7443, to $X_1$, e.g. in Structure B, or to X or Y, e.g., in Structure C, or D.

In certain embodiments, a compound comprising a conjugated modified oligonucleotide described herein has Structure A:

La-linker-MO;

wherein each L is, independently, a ligand and n is from 1 to 10; and MO is RG7443.

In some embodiments, a compound has the structure:

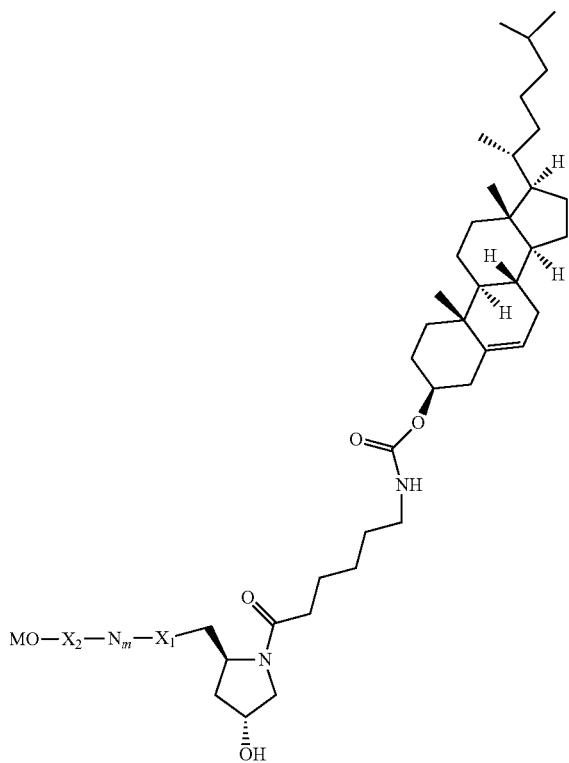

wherein each N is, independently, a modified or unmodified nucleoside and m is from 1 to 5; $X_1$ and $X_2$ are each, independently, a phosphodiester linkage or a phosphorothioate linkage; and MO is RG7443.

In certain embodiments, at least one of $X_1$ and $X_2$ is a phosphodiester linkage. In certain embodiments, each of $X_1$ and $X_2$ is a phosphodiester linkage.

In certain embodiments, m is 1. In certain embodiments, m is 2. In certain embodiments, m is 3, 4, or 5. In certain embodiments, m is 2, 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or a phosphorothioate internucleoside linkage.

In any of the embodiments described herein, $N_m$ may be $N'_pN''$, where each N' is, independently, a modified or unmodified nucleoside and p is from 0 to 4; and N" is a nucleoside comprising an unmodified sugar moiety.

In certain embodiments, p is 0. In certain embodiments, p is 1, 2, 3, or 4. In certain embodiments, when p is 1, 2, 3, or 4, each N' comprises an unmodified sugar moiety.

In certain embodiments, an unmodified sugar moiety is a β-D-ribose or a β-D-deoxyribose.

In certain embodiments, where p is 1, 2, 3, or 4, N' comprises a purine nucleobase. In certain embodiments, N" comprises a purine nucleobase. In certain embodiments, a purine nucleobase is selected from adenine, guanine, hypoxanthine, xanthine, and 7-methylguanine. In certain embodiments, N' is a β-D-deoxyriboadenosine or a β-D-deoxyriboguanosine. In certain embodiments, N" is a β-D-deoxyriboadenosine or a β-D-deoxyriboguanosine.

In certain embodiments, p is 1, N' and N" are each a 3-D-deoxyriboadenosine, and N' and N" are linked by a phosphodiester internucleoside linkage. In certain embodiments, p is 1, N' and N" are each a O-D-deoxyriboadenosine, and N' and N" are linked by a phosphodiester internucleoside linkage. In certain embodiments, p is 1, N' and N" are each a β-D-deoxyriboadenosine, and N' and N" are linked by a phosphorothioate internucleoside linkage.

In certain embodiments, where p is 1, 2, 3, or 4, N' comprises a pyrimidine nucleobase. In certain embodiments, N" comprises a pyrimidine nucleobase. In certain embodiments, a pyrimidine nucleobase is selected from cytosine, 5-methylcytosine, thymine, uracil, and 5,6-dihydrouracil.

In certain embodiments, the sugar moiety of each N is independently selected from a β-D-ribose, a β-D-deoxyribose, a 2'-O-methoxy sugar, a 2'-O-methyl sugar, a 2'-fluoro sugar, and a bicyclic sugar moiety. In certain embodiments, each bicyclic sugar moiety is independently selected from a cEt sugar moiety, an LNA sugar moiety, and an ENA sugar moiety. In certain embodiments, the cEt sugar moiety is an S-cEt sugar moiety. In certain embodiments, the cEt sugar moiety is an R-cEt sugar moiety.

In certain embodiments, a compound comprises a conjugate moiety linked to the 5' terminus of the modified oligonucleotide. In certain embodiments, a compound comprises a conjugate moiety linked to the 3' terminus of the modified oligonucleotide. In certain embodiments, a compound comprises a conjugate moiety linked to the 5' terminus of the modified oligonucleotide. In certain embodiments, a compound comprises a first conjugate moiety linked to the 3' terminus of the modified oligonucleotide and a second conjugate moiety linked to the 5' terminus of the modified oligonucleotide.

Certain Metabolic Products

Upon exposure to exonucleases and/or endonucleases in vitro or in vivo, compounds may undergo cleavage at various positions throughout the compound. The products of such cleavage may retain some degree of the activity of the parent compound, and as such are considered active metabolites. As such, a metabolic product of a compound may be used in the methods described herein. In certain embodiments, a modified oligonucleotide (unconjugated or conjugated) undergoes cleavage at the 5' end and/or the 3' end, resulting in a metabolic product that has 1, 2, or 3 fewer nucleotides at the 5' end and/or the 3' end, relative to the parent modified oligonucleotide. In certain embodiments, a modified oligonucleotide undergoes cleavage at the 5' end, releasing the 5'-terminal nucleotide and resulting in a metabolic product that has 1 less nucleotide at the 5' end, relative to the parent modified oligonucleotide. In certain embodiments, a modified oligonucleotide undergoes cleavage at the 5' end, releasing two 5'-terminal nucleosides and resulting in a metabolic product that has two fewer nucleotides at the 5' end, relative to the parent modified oligonucleotide. In certain embodiments, a modified oligonucleotide undergoes cleavage at the 3' end, releasing the 3'-terminal nucleotide and resulting in a metabolic product that has one less nucleotide at the 3' end, relative to the parent modified oligonucleotide. In certain embodiments, a modified oligonucleotide undergoes cleavage at the 3' end, releasing two 3'-terminal nucleosides and resulting in a metabolic product that has two fewer nucleotides at the 3' end, relative to the parent modified oligonucleotide.

Compounds comprising modified oligonucleotide linked to a conjugate moiety may also undergo cleavage at a site within the linker between the modified oligonucleotide and the ligand. In certain embodiments, cleavage yields the parent modified oligonucleotide comprising a portion of the conjugate moiety. In certain embodiments, cleavage yields the parent modified oligonucleotide comprising one or more subunits of the linker between the modified oligonucleotide and the ligand. For example, where a compound has the structure $L_n$-linker-$X_1$—$N_m$—$X_2$-MO, in some embodiments, cleavage yields the parent modified oligonucleotide comprising one or more nucleotides of $N_m$. In some embodiments, cleavage of a conjugated modified oligonucleotide yields the parent modified oligonucleotide. In some such embodiments, for example, where a compound has the structure $L_n$-linker-$X_1$—$N_m$—$X_2$-MO, in some embodiments, cleavage yields the parent modified oligonucleotide without any of the nucleotides of $N_m$.

Certain Nucleobase Sequences

Any anti-miR-122 nucleobase sequences set forth herein, including but not limited to those found in the examples and in the sequence listing, are independent of any modification to the nucleic acid. As such, nucleic acids defined by a SEQ ID NO may comprise, independently, one or more modifications to one or more sugar moieties, to one or more internucleoside linkages, and/or to one or more nucleobases.

Although the sequence listing accompanying this filing identifies each nucleobase sequence as either "RNA" or "DNA" as required, in practice, those sequences may be modified with any combination of chemical modifications. One of skill in the art will readily appreciate that such designation as "RNA" or "DNA" to describe modified oligonucleotides is somewhat arbitrary. For example, a modified oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to, those in the sequence listing, are intended to encompass nucleic acids containing any combination of natural or modified RNA and/or DNA, including, but not limited to such nucleic acids having modified nucleobases. By way of further example and without limitation, a modified oligonucleotide having the nucleobase sequence "ATCGATCG" encompasses any oligonucleotide having such nucleobase sequence, whether modified or unmodified, including, but not limited to, such compounds comprising RNA bases, such as those having sequence "AUCGAUCG" and those having some DNA bases and some RNA bases such as "AUCGATCG" and oligonucleotides having other modified bases, such as "AT$^{me}$CGAUCG," wherein $^{me}$C indicates a 5-methylcytosine. Similarly, a modified oligonucleotide having the nucleobase sequence "AUCGAUCG" encompasses any oligonucleotide having such nucleobase sequence, whether modified or unmodified, including, but not limited to, such compounds comprising DNA bases, such as those having sequence "ATCGATCG" and those having some DNA bases and some RNA bases such as "AUCGATCG" and oligonucleotides having other modified bases, such as "AT$^{me}$CGAUCG," wherein $^{me}$C indicates a 5-methylcytosine.

Certain Modifications

A modified oligonucleotide may comprise one or more modifications to a nucleobase, sugar, and/or internucleoside linkage. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

In certain embodiments, a modified oligonucleotide comprises one or more modified nucleosides. In certain embodiments, a modified nucleoside is a stabilizing nucleoside. An example of a stabilizing nucleoside is a 2'-modified nucleoside.

In certain embodiments, a modified nucleoside comprises a modified sugar moiety. In certain embodiments, a modified nucleoside comprising a modified sugar moiety comprises an unmodified nucleobase. In certain embodiments, a modified sugar comprises a modified nucleobase. In certain embodiments, a modified nucleoside is a 2'-modified nucleoside.

In certain embodiments, a 2'-modified nucleoside comprises a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

In certain embodiments, the bicyclic sugar moiety comprises a bridge group between the 2' and the 4'-carbon atoms. Nucleosides comprising bicyclic sugar moieties are referred to as bicyclic nucleosides or BNAs. In certain embodiments, bicyclic nucleosides include, but are not limited to, (A) α-L-Methyleneoxy (4'-CH$_2$—O-2') BNA; (B) β-D-Methyleneoxy (4'-CH$_2$—O-2') BNA; (C) Ethyleneoxy (4'—(CH$_2$)$_2$—O-2') BNA; (D) Aminooxy (4'-CH$_2$—O—N(R)-2') BNA; (E) Oxyamino (4'-CH$_2$—N(R)—O-2') BNA; (F) Methyl(methyleneoxy) (4'-CH(CH$_3$)—O-2') BNA (also referred to as constrained ethyl or cEt); (G) methylene-thio (4'-CH$_2$—S-2') BNA; (H) methylene-amino (4'-CH2-N(R)-2') BNA; (I) methyl carbocyclic (4'-CH$_2$—CH(CH$_3$)-2') BNA; (J) c-MOE (4'-CH$_2$—OMe-2') BNA and (K) propylene carbocyclic (4'—(CH$_2$)$_3$-2') BNA as depicted below.

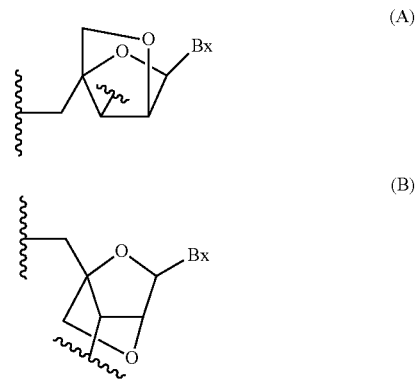

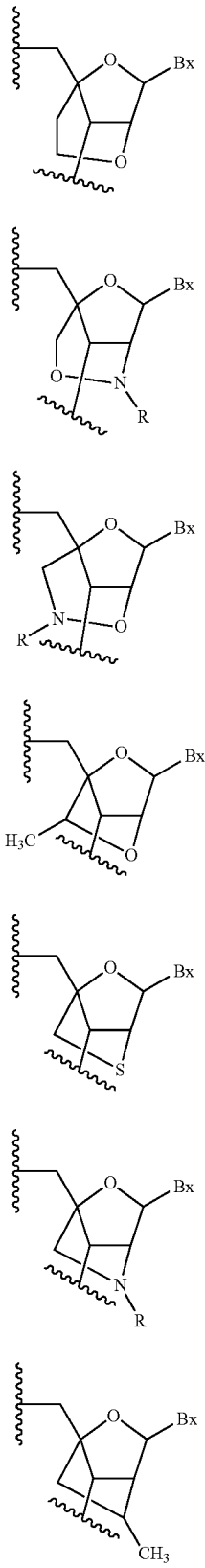

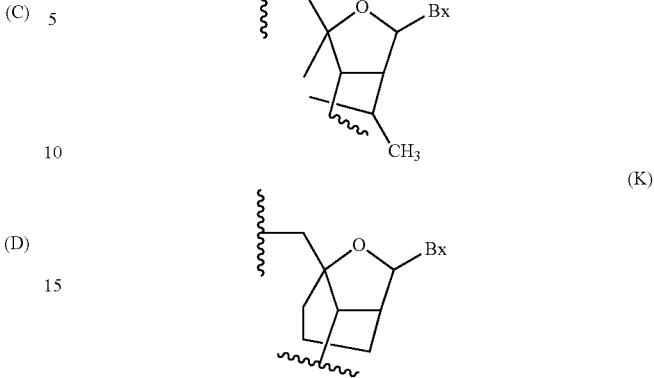

wherein Bx is a nucleobase moiety and R is, independently, H, a protecting group, or $C_1$-$C_{12}$ alkyl.

In certain embodiments, a 2'-modified nucleoside comprises a 2'-substituent group selected from F, $OCF_3$, O—$CH_3$, $OCH_2CH_2OCH_3$, 2'-O$(CH_2)_2SCH_3$, O—$(CH_2)_2$—O—$N(CH_3)_2$, —O$(CH_2)_2$O$(CH_2)_2$N$(CH_3)_2$, and O—$CH_2$—C(=O)—N(H)$CH_3$.

In certain embodiments, a 2'-modified nucleoside comprises a 2'-substituent group selected from F, O—$CH_3$, and $OCH_2CH_2OCH_3$.

In certain embodiments, a modified oligonucleotide comprises one or more internucleoside modifications. In certain such embodiments, each internucleoside linkage of a modified oligonucleotide is a modified internucleoside linkage. In certain embodiments, a modified internucleoside linkage comprises a phosphorus atom.

In certain embodiments, a modified oligonucleotide comprises at least one phosphorothioate internucleoside linkage. In certain embodiments, each internucleoside linkage of a modified oligonucleotide is a phosphorothioate internucleoside linkage.

In certain embodiments, a modified oligonucleotide comprises one or more modified nucleobases. In certain embodiments, a modified nucleobase is selected from 7-deazaguanine, 7-deazaadenine, hypoxanthine, xanthine, 7-methylguanine, 2-aminopyridine and 2-pyridone. In certain embodiments, a modified nucleobase is selected from 5-substituted pyrimidines, 6-azapyrimidines and N-2, N-6 and 0-6 substituted purines, including 2 aminopropyladenine, 5-propynyluracil and 5-propynylcytosine.

Certain Synthesis Methods

Modified oligonucleotides may be made with automated, solid phase synthesis methods known in the art. During solid phase synthesis, phosphoramidite monomers are sequentially coupled to a nucleoside that is covalently linked to a solid support. This nucleoside is the 3' terminal nucleoside of the modified oligonucleotide. Typically, the coupling cycle comprises four steps: detritylation (removal of a 5'-hydroxyl protecting group with acid), coupling (attachment of an activated phosphoroamidite to the support bound nucleoside or oligonucleotide), oxidation or sulfurization (conversion of a newly formed phosphite trimester with an oxidizing or sulfurizing agent), and capping (acetylation of unreacted 5'-hydroxyl groups). After the final coupling cycle, the solid support-bound oligonucleotide is subjected to a detritylation step, followed by a cleavage and deprotection step that simultaneously releases the oligonucleotide from the solid support and removes the protecting groups from the bases. The solid support is removed by filtration, the filtrate is concentrated and the resulting solution is tested for identity and purity. The oligonucleotide is then purified, for example using a column packed with anion-exhange resin.

GalNAc-conjugated modified oligonucleotides may be made with automated solid phase synthesis, similar to the solid phase synthesis that produced unconjugated oligonucleotides. During the synthesis of GalNAc-conjugated oligonucleotides, the phosphoramidite monomers are sequentially coupled to a GalNAc conjugate which is covalently linked to a solid support. The synthesis of GalNAc conjugates and GalNAc conjugate solid support is described, for example, in U.S. Pat. No. 8,106,022, and International Application Publication No. WO 2013/033230, each of which is herein incorporated by reference in its entiretly for the description of the synthesis of carbohydrate-containing conjugates, including conjugates comprising one or more GalNAc moieties, and of the synthesis of conjugate covalently linked to solid support.

Certain Pharmaceutical Compositions Provided herein are pharmaceutical compositions comprising a compound provided herein, and a pharmaceutically acceptable diluent. In certain embodiments, the pharmaceutically acceptable diluent is an aqueous solution. In certain embodiments, the aqueous solution is a saline solution. As used herein, pharmaceutically acceptable diluents are understood to be sterile diluents. Suitable administration routes include, without limitation, intravenous and subcutaneous administration.

In certain embodiments, a pharmaceutical composition is a compound provided herein which has been prepared in a suitable diluent, adjusted to pH 7.0-9.0 with acid or base during preparation, and then lyophilized under sterile conditions. The lyophilized modified oligonucleotide is subsequently reconstituted with a suitable diluent, e.g., aqueous solution, such as water or physiologically compatible buffers such as saline solution, Hanks's solution, or Ringer's solution. The reconstituted product is administered as a subcutaneous injection or as an intravenous infusion. The lyophilized drug product may be packaged in a 2 mL Type I, clear glass vial (ammonium sulfate-treated), stoppered with a bromobutyl rubber closure and sealed with an aluminum overseal.

In certain embodiments, a pharmaceutical composition is administered in the form of a dosage unit (e.g., tablet, capsule, bolus, etc.). In some embodiments, a pharmaceutical composition comprises a compound provided herein at a dose within a range selected from 25 mg to 250 mg. In certain embodiments, such pharmaceutical compositions comprise a compound provided herein present at a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, or 250 mg.

Pharmaceutical compositions may also contain suitable stabilizers or agents that increase the solubility of the pharmaceutical agents to allow for the preparation of highly concentrated solutions.

In certain embodiments, the pharmaceutical compositions provided herein may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents.

Certain miR-122 Kits

The present invention also provides kits. In some embodiments, the kits comprise one or more compounds provided herein. In some embodiments, a compound provided herein is present within a vial. A plurality of vials, such as 10, can be present in, for example, dispensing packs. In some embodiments, the vial is manufactured so as to be accessible with a syringe. The kit can also contain instructions for using the compounds provided herein.

In some embodiments, the kits may be used for administration of a compound provided herein to a subject. In such instances, in addition to comprising at least one compound provided herein, the kit can further comprise one or more of the following: syringe, alcohol swab, cotton ball, and/or gauze pad. In some embodiments, the compounds complementary to miR-122 can be present in a pre-filled syringe (such as a single-dose syringes with, for example, a 27 gauge, ½ inch needle with a needle guard), rather than in a vial. A plurality of pre-filled syringes, such as 10, can be present in, for example, dispensing packs. The kit can also contain instructions for administering a compound provided herein.

Certain Experimental Models

In certain embodiments, the present invention provides methods of using and/or testing a compound provided herein in an experimental model. Those having skill in the art are able to select and modify the protocols for such experimental models to evaluate a compound provided herein.

The effects of antisense inhibition of a microRNA following the administration of anti-miR compounds may be assessed by a variety of methods known in the art. In certain embodiments, these methods are used to quantitate microRNA levels in cells or tissues in vitro or in vivo. In certain embodiments, changes in microRNA levels are measured by microarray analysis. In certain embodiments, changes in microRNA levels are measured by one of several commercially available PCR assays, such as the TaqMan® MicroRNA Assay (Applied Biosystems, a Life Technologies brand).

In vitro activity of anti-miR compounds may be assessed using a luciferase cell culture assay. In this assay, a microRNA luciferase sensor construct is engineered to contain one or more binding sites of the microRNA of interest fused toa luciferase gene. When the microRNA binds to its cognate site in the luciferase sensor construct, luciferase expression is suppressed. When the appropriate anti-miR is introduced into the cells, it binds to the target microRNA and relieves suppression of luciferase expression. Thus, in this assay anti-miRs that are effective inhibitors of the microRNA of interest will cause an increase in luciferase expression.

Activity of anti-miR compounds may be assessed by measuring the mRNA and/or protein level of a target of a microRNA. A microRNA binds to a complementary site within one or more target RNAs, leading to suppression of a target RNA, thus inhibition of the microRNA results in the increase in the level of mRNA and/or protein of a target of the microRNA (i.e., derepression). The derepression of one or more target RNAs may be measured in vivo or in vitro. For example, a target of miR-122 is aldolase A (ALDOA). Inhibition of miR-122 results in an increase in the level of ALDOA mRNA, thus ALDOA mRNA levels may be used to evaluate the inhibitory activity of an anti-miR-122 compound.

The effects of anti-miR-122 compounds on HCV replication may be measured in an HCV replicon assay. In this assay, compounds are introduced into a cell line (e.g., a human hepatoma cell line) that contains a subgenomic replicon of HCV with a stable luciferase reporter and three cell culture-adaptive mutations (luc-ubi-neo/ET). The luciferase reporter is used as an indirect measure of HCV replication. The replicon used may be a parent HCV genotype or an HCV genotype with mutations that confer resistance to anti-viral agents. Anti-miR-122 compounds may be evaluated alone or in combination with other agents used in the treatment of HCV-infection. In some embodiments, a modified oligonucleotide may be tested in an in vivo or in vitro assay, and subsequently conjugated to form a compound for use in the methods described herein.

EXAMPLES

The following examples are presented in order to more fully illustrate some embodiments of the invention. They should, in no way be construed, however, as limiting the broad scope of the invention. Those of ordinary skill in the art will readily adopt the underlying principles of this discovery to design various compounds without departing from the spirit of the current invention.

Example 1: Anti-miR-122 Compounds for the Treatment of HCV Infection miR-122, a microRNA abundantly and specifically expressed in the liver, is a critical host factor for hepatitis C virus accumulation (Jopling et al., Science. 2005, 309 (5740), 1577-81). miR-122 interacts with HCV by binding to two closely spaced seed sequence sites in the 5' noncoding region of the HCV genome, resulting in stabilization of the HCV genome, supporting replication and translation (Jangra et al., J Virol., 2010, 84: 6615-6625; Machlin, et al., 2011). RG-101 is a GalNAc-conjugated modified oligonucleotide targeted to miR-122.

In a completed Phase I human proof-of-concept study, treatment with a single subcutaneous dose of RG-101 as monotherapy resulted in significant and sustained viral load reductions in all treated HCV-infected subjects, including subjects with difficult to treat genotypes, various liver fibrosis status and those who have experienced viral relapse after a prior IFN-containing regimen.

In a completed Phase II study evaluating the combination of RG-101 with multiple approved direct-acting antiviral (DAA) drugs, subjects received a single subcutaneous injection of 2 mg/kg of RG-101 on Day 1, followed by 28 days of a once daily oral DAA (Harvoni®, Olysio®, or Daklinza™) followed by an additional subcutaneous injection of 2 mg/kg of RG-101 on Day 29. Virological response was defined as HCV RNA viral load below lower limit of quantitation (LLOQ) using RealTime HCV Assay (Abbott) with LLOQ=12 IU/mL. The number and percentage of subjects with a virological response is shown in Table 1. Notably, all subjects in the RG-101+Harvoni group experienced a significant and sustained viral load reduction throughout the 48-week follow up period. In the RG-101+ Olysio group and the RG-101+Daklinza groups, 6 and 4 subjects experienced a relapse, respectively. In the RG-101+ Olysio group, one subject withdrew consent so was not included in the Week 48 time point.

TABLE 1

| Virological Response Following Treatment with RG-101 + DAA | | | |
| --- | --- | --- | --- |
| Week of Follow-up | RG-101 + Harvoni | RG-101 + Olysio | RG-101 + Daklinza |
| Week 12 | 27/27 (100%) | 26/27 (96.3%) | 22/25 (88.0%) |
| Week 24 | 27/27 (100%) | 23/27 (85.2%) | 22/25 (88.0%) |
| Week 48 | 27/27 (100%) | 20/27 (76.9%) | 21/25 (84.0%) |

During the Phase 2 study, 10 of 200 subjects experienced transient hyperbilirubinemia, characterized by increased conjugated and total bilirubin above the upper limit of normal (ULN). The U.S. Food and Drug Administration placed the IND for RG-101 for the treatment of chronic HCV infection on clinical hold.

To identify the mechanism underlying the hyperbilirubinemia, literatures searches were conducted, and preclinical data from RG-101 studies was thoroughly re-analyzed. Literature searches revealed no previously reported association between miR-122 and bilirubin metabolism pathways, or between oligonucleotides as a class of drugs and bilirubin metabolism pathways. Among the numerous studies conducted in mice, rats, and monkeys, at doses substantially higher than the tested clinical doses, no cases of increase bilirubin were identified. Further, during the pre-IND stage, RG-101 and its active metabolite were tested for their ability to interact with cytochrome P450 enzymes and uptake and efflux transporters. As expected for oligonucleotides, neither compound interacted significantly with these enzymes and transporters.

It was hypothesized that interference with a bilirubin transporter in the liver could lead to hyperbilirubinemia. There are several transporters in the liver that participate in the transport of bilirubin between hepatocytes and bile. One such transporter, the multidrug resistance-associated protein 2 (MRP2), is encoded by the ABCC2 gene and is expressed on the apical side of hepatocytes, the apical membrane of proximal renal tubular cells, and the intestinal lumen (enterocytes). The MRP2 transporter is involved in the exretion of organic anions such as conjugated bilirubin. Known inhibitors of the MRP2 transporter include probenecid, furosemide, ritonavir, abacavir, cyclosporin A, and tenofovir. However, as noted above, oligonucleotides have not previously been reported as inhibitors of MRP2.

An additional factor contributing to hyperbilirubinemia may be the level of MRP2 expression in HCV-infected subjects. MRP2 expression is reduced in HCV-infected subjects by approximately 70%, relative to non-infected subjects (J Hepatol. 2001 December; 35(6):765-73). Accordingly, HCV-infected subjects may be more susceptible to the effects of a compound that inhibits MRP2 transporter activity, as the levels of MRP2 are already reduced in these subjects. Further, MRP2 expression is lower in humans than in rodents and non-human primates, which may explain why hyperbilirubinemia was not observed in preclinical or IND-enabling studies.

To test the hypothesis that RG-101 was interfering with MRP2 transporter activity, an in vitro assay was performed per methods known in the art (see, for example, Vermeer et al., Drug Metab. Dispos., 2016, 44(3):453-9). In this assay, an efflux transporter-expressing vesicle is used to evaluate if a drug is a substrate or inhibitor of a transporter. Inside-out membrane vesicles are prepared from insect cells transiently transfected with a single efflux transporter, in this case MRP2. As the vesicles are in an inside-out orientation, the MRP2 transporter pumps radiolabeled substrate, [3H]-estradiol-17β-glucuronide, in an ATP-dependent manner, into the vesicles, and the accumulation of radiolabeled substrate inside the vesicle is measured. If a compound is an MRP2 transport inhibitor, the accumulation of radiolabeled substrate will be reduced relative to control samples. The inhibitory effect of the compound is evaluated by determining the IC50, the concentration resulting in 50% inhibition of transporter-mediated uptake of the radiolabeled substrate.

The in vitro MRP2 assay was performed for RG-101. Both RG-101, and RG1649, the unconjugated anti-miR of RG-101, were tested at concentrations of 0, 0.1, 0.3, 1, 3, 10, 30, and 100 uM. The calculated IC50 values were 5.98 uM and 2.21 uM for RG-101 and RG1649, respectively. Thus, RG-101 inhibited the MPR2 transporter in this assay. Additional studies were conducted, confirming that both RG-101 and RG1649 inhibit the MRP2 transporter in this assay (RG-101 IC50 ranged from 5 to 62 uM; RG1649 IC50 ranged from 2 to 11 uM.

While additional HCV-infected subject-specific contributing factors cannot be definitively excluded, based in part on the MRP2 assay data, it is believed that a combination of factors including inhibition of conjugated bilirubin transport by RG-101, impaired baseline bilirubin transport in HCV-infected subjects and the preferential uptake of RG-101 by hepatocytes (due to the GalNAc conjugate moiety) likely contributed to the observed hyperbilirubinemia. In view of this, a screen was conducted for alternative compounds targeting miR-122 that maintain potent HCV antiviral activity, but do not significantly interfere with bilirubin transport via the MRP2 transporter.

Example 2: In Vitro Screening for Potent Anti-miR-122 Compounds Lacking Significant MRP2 Inhibition Anti-miR-122 compounds were selected for testing to evaluate HCV replicon inhibition, MRP2 transporter inhibition, in vitro and in vivo safety, in vivo pharmacodynamic potency, and in vivo efficacy in a mouse model of HCV infection. These compounds varied in length, nucleoside sugar modifications, and internucleoside linkage modifications. Additionally, both unconjugated and GalNAc-conjugated compounds were tested.

HCV Replicon Studies

An HCV replicon assay was used to determine the ability of anti-miR-122 compounds to inhibit the replication of HCV genotype 1b. In this assay, test compounds are introduced into Huh7 cells stably transfected with a HCV GT1b replicon containing a luciferase reporter gene. The luciferase reporter is used as an indirect measure of HCV replication. While a GalNAc-conjugated compound is expected to be preferable for treatment of HCV infection, due to the enhanced delivery to hepatocytes, some unconjugated compounds were tested.

Selected compounds were tested at nine concentrations ranging from 0.015 uM to 100 uM. GS-7977 (sofosbuvir) was included as a positive control. Cells were plated into 96-well plates at a density of 8,000 cells per well. Compound was added to the cells for a period of 72 hours. Luminescent signal in the supernatant was detected using the Bright-Glo reagent, and used to calculate the antiviral activity of each compound. The CellTiter-Fluor reagent was used to assess cell viability. The $EC_{50}$ (concentration at which 50% inhibition was observed) was calculated.

Certain anti-miR-122 compounds tested in the replicon assay, and their calculated EC50 values, are shown in Table 2. Nucleosides not followed by a subscript indicate β-D-deoxyribonucleosides; nucleosides followed by a subscript "E" indicate 2'-MOE nucleosides; nucleosides followed by a subscript "S" indicate S-cEt nucleosides. Phosphodiester linkages are indicated by "PO"; all other linkages are phosphorothioate. "Me" indicates a 5-methyl group on the base of the nucleoside.

As illustrated in Table 2, variations in length, nucleoside sugar modifications and/or internucleoside linkages lead to differences in viral inhibition. For example, RG3054 contains a single additional nucleoside at the 5' end relative to RG2634, yet RG3054 is substantially less potent than RG2634. RG6371 and RG6370 differ only in the number of phosphodiester vs phosphorothioate internucleoside linkages yet exhibited different potencies. Of the GalNAc-conjugated compounds, RG6650 and RG2634 were the most potent in this assay. While RG6234 and RG497998 are potent in this in vitro assay, as unconjugated compounds, in vivo potency is not expected to be suitable for use as a therapeutic agent.

Certain compounds were tested in multiple experiments. The EC50 for RG-101 ranged from 1.994 to 10.68 uM. The EC50 for RG2634 ranged from 13.93 to 31.1 uM. The EC50 for RG6650 ranged from 7.716 to 11.3 uM. The EC50 for RG497998 ranged from 7.708 to 10.87 uM.

TABLE 2

Anti-miR-122 Compounds in HCV Replicon Assay

| Compound | Modified Oligonucleotide | $X_2$ | N | $X_1$ | Conjugate | EC50 uM Expt #1 | EC50 uM Expt #2 |
|---|---|---|---|---|---|---|---|
| RG-101 | $A_E{}^{Me}C_E A_E{}^{Me}C_E{}^{Me}C_E A_E T_E TGU_S C_S AC_S AC_S TC_S C_S$ (SEQ ID NO: 2) | PO | A | PO | GalNAc(3) | 2.079 | 5.007 |
| RG1649 | $A_E{}^{Me}C_E A_E{}^{Me}C_E{}^{Me}C_E A_E T_E TGU_S C_S AC_S AC_S TC_S C_S$ (SEQ ID NO: 2) | | | | | | 0.7196 |
| RG6650 | $U_S C_S AC_S AC_S TC_S C_S$ | PO | A | PO | GalNAc(3) | | 11.30 |
| RG2634 | $C_S A_S C_S A_S C_S U_S C_S C_S$ | PO | A | PO | GalNAc(3) | 22.47 | |
| RG3054 | $U_S C_S A_S C_S A_S C_S U_S C_S C_S$ | PO | A | PO | GalNAc(3) | >100 | |
| RG6370 | $CsA_S C_S A_S C_S U_S C_S C_S A_S$ | PO | A | PO | GalNAc(3) | 60.92 | |
| RG6371 | $C_S A_S C_S{}^{PO} A_S{}^{PO} C_S{}^{PO} U_S{}^{PO} C_S C_S A_S$ | PO | A | PO | GalNAc(3) | 34.11 | |

TABLE 2-continued

Anti-miR-122 Compounds in HCV Replicon Assay

| Compound | Modified Oligonucleotide | $X_2$ | N | $X_1$ | Conjugate | EC50 uM Expt #1 | EC50 uM Expt #2 |
|---|---|---|---|---|---|---|---|
| RG6372 | $U_SC_SA_S{}^{PO}C_S{}^{PO}A_S{}^{PO}C_S{}^{PO}U_SC_SC_S$ | PO | A | PO | GalNAc(3) | >100 | |
| RG6234 | $C_SA_SC_SA_SC_SU_SC_SC_SA_S$ | | | | None | 17.42 | |
| RG497998 | $C_SA_SC_SA_SC_SU_SC_SC_S$ | | | | None | 7.708 | |
| GS-7977 | | | | | Not applicable | 0.149 | 0.098 |

The MRP2 assay was performed for anti-miR-122 compounds selected based on potency in the HCV replicon assay and structural diversity. As shown in Table 3, RG-101 and RG1649 inhibited MRP2 transporter activity in this assay. RG6650, RG2634, RG3054, RG6370, RG6234, and RG497998 each exhibited an $IC_{50}$ of greater than 100 uM, indicating that these compounds do not significantly interfere with MRP2 transporter activity in this assay.

For some compounds, the assay was conducted multiple times. The RG1649 IC50 ranged from 2 to 11 uM, and the RG-101 IC50 ranged from 5 to 62. The RG6650 was greater than 100 uM each time this compound was tested.

A (ALDOA), a gene that is normally suppressed by miR-122 activity. Inhibition of miR-122 leads to an increase in ALDOA expression, thus ALDOA mRNA levels can be used to measure miR-122 inhibitory activity in vivo.

Only GalNAc-conjugated compounds were tested in this assay. Compounds were administered at molar equivalents with regard to the anti-miR portion of the compound. A single, subcutaneous dose of RG-101 was administered subcutaneously at doses ranging from 0.004 to 1.116 umol/kg. Other compounds were administered in a single subcutaneous dose at doses ranging from 0.006 to 1.942 umol/kg.

TABLE 3

Anti-miR-122 Compounds in MRP2 Transporter Assay

| Compound | Modified Oligonucleotide | $X_2$ | N | $X_1$ | Conjugate | IC50 uM Expt #1 | IC50 uM Expt #2 |
|---|---|---|---|---|---|---|---|
| RG-101 | $A_E{}^{Me}C_EA_E{}^{Me}C_E{}^{Me}C_EA_ET_ETGU_SC_SAC_SAC_STC_SC_S$ (SEQ ID NO: 2) | PO | A | PO | GalNAc(3) | 5.98 | |
| RG1649 | $A_E{}^{Me}C_EA_E{}^{Me}C_E{}^{Me}C_EA_ET_ETGU_SC_SAC_SAC_STC_SC_S$ (SEQ ID NO: 2) | | | | | 2.21 | |
| RG6650 | $U_SC_SAC_SAC_STC_SC_S$ | PO | A | PO | GalNAc(3) | >100 | |
| RG2634 | $C_SA_SC_SA_SC_SU_SC_SC_S$ | PO | A | PO | GalNAc(3) | | >100 |
| RG3054 | $U_SC_SA_SC_SA_SC_SU_SC_SC_S$ | PO | A | PO | GalNAc(3) | | >100 |
| RG6370 | $CsA_SC_SA_SC_SU_SC_SC_SA_S$ | PO | A | PO | GalNAc(3) | | >100 |
| RG6371 | $C_SA_SC_S{}^{PO}A_S{}^{PO}C_S{}^{PO}U_S{}^{PO}C_SC_SA_S$ | PO | A | PO | GalNAc(3) | ND | ND |
| RG6372 | $U_SC_SA_S{}^{PO}C_S{}^{PO}A_S{}^{PO}C_S{}^{PO}U_SC_SC_S$ | PO | A | PO | GalNAc(3) | ND | ND |
| RG6234 | $C_SA_SC_SA_SC_SU_SC_SC_SA_S$ | | | | None | | >100 |
| RG497998 | $C_SA_SC_SA_SC_SU_SC_SC_S$ | | | | None | | >100 |
| GS-7977 | | | | | Not applicable | ND | ND |

Example 3: In Vivo Screening for Potent Anti-miR-122 Compounds Lacking MRP2 Inhibition Compounds that inhibited HCV replication in the replicon assay, and did not inhibit MRP32 in the in vitro transporter assay, were further tested for in vivo potency and safety. Potency To determine in vivo potency, compounds were evaluated for their ability to de-repress the expression of liver aldolase After 7 days the study was terminated. Liver tissue was collected for measurement of ALDOA mRNA and drug levels. Kidney tissue was collected for measurement of drug levels. Blood was collected for measurement of cholesterol.

ALDOA mRNA levels were measured, by quantitative PCR, in RNA isolated from liver. The fold change in ALDOA mRNA, relative to saline, was used to calculate an ED50 (umol/kg) for each compound ("ND" indicates "not determined), as shown in Table 4.

With the exception of RG6370 (and RG3054 where the results were not interpretable), for ALDOA derepression (Table 4) each compound tested in this assay exhibited an ED50 similar to RG-101.

For cholesterol reduction (Table 5), each compound tested exhibited an ED50 similar to or better than RG-101.

with compound at doses ranging from 0.014 to 1.117 umol/kg. Liver tissue was collected from groups of 4 to 5 mice 1, 3, 7, or 14 days following administration. RNA was isolated and ALDOA mRNA was measured. It was observed that RG6650 exhibited an increased de-repression of ALDOA mRNA at a lower dose and earlier time point, relative to

TABLE 4

ALDOA Derepression

| Compound | Modified Oligonucleotide | $X_2$ | N | $X_1$ | Conjugate | ED50 Expt #1 | ED50 Expt #2 |
|---|---|---|---|---|---|---|---|
| RG-101 | $A_E{}^{Me}C_EA_E{}^{Me}C_E{}^{Me}C_EA_ET_ETGU_SC_SAC_SAC_STC_SC_S$ (SEQ ID NO: 2) | PO | A | PO | GalNAc(3) | 0.041 | 0.122 |
| RG6650 | $U_SC_SAC_SAC_STC_SC_S$ | PO | A | PO | GalNAc(3) |  | 0.091 |
| RG2634 | $C_SA_SC_SA_SC_SU_SC_SC_S$ | PO | A | PO | GalNAc(3) | 0.029 |  |
| RG3054 | $U_SC_SA_SC_SA_SC_SU_SC_SC_S$ | PO | A | PO | GalNAc(3) | * |  |
| RG6370 | $CsA_SC_SA_SC_SU_SC_SC_SA_S$ | PO | A | PO | GalNAc(3) | 6.51 |  |
| RG6371 | $C_SA_SC_S{}^{PO}A_S{}^{PO}C_S{}^{PO}U_S{}^{PO}C_SC_SA_S$ | PO | A | PO | GalNAc(3) | 0.086 |  |
| RG6372 | $U_SC_SA_S{}^{PO}C_S{}^{PO}A_S{}^{PO}C_S{}^{PO}U_SC_SC_S$ | PO | A | PO | GalNAc(3) | 0.028 |  |

*Results not interpretable

TABLE 5

Cholesterol Reduction

| Compound | Modified Oligonucleotide | $X_2$ | N | $X_1$ | Conjugate | ED50 Expt #1 | ED50 Expt #2 |
|---|---|---|---|---|---|---|---|
| RG-101 | $A_E{}^{Me}C_EA_E{}^{Me}C_E{}^{Me}C_EA_ET_ETGU_SC_SAC_SAC_STC_SC_S$ (SEQ ID NO: 2) | PO | A | PO | GalNAc(3) | 1.104 | 0.079 |
| RG6650 | $U_SC_SAC_SAC_STC_SC_S$ | PO | A | PO | GalNAc(3) |  | 0.025 |
| RG2634 | $C_SA_SC_SA_SC_SU_SC_SC_S$ | PO | A | PO | GalNAc(3) | 0.011 |  |
| RG3054 | $U_SC_SA_SC_SA_SC_SU_SC_SC_S$ | PO | A | PO | GalNAc(3) | .08152 |  |
| RG6370 | $CsA_SC_SA_SC_SU_SC_SC_SA_S$ | PO | A | PO | GalNAc(3) | 0.0007 |  |
| RG6371 | $C_SA_SC_S{}^{PO}A_S{}^{PO}C_S{}^{PO}U_S{}^{PO}C_SC_SA_S$ | PO | A | PO | GalNAc(3) | 1.116 |  |
| RG6372 | $U_SC_SA_S{}^{PO}C_S{}^{PO}A_S{}^{PO}C_S{}^{PO}U_SC_SC_S$ | PO | A | PO | GalNAc(3) | 0.8088 |  |

Safety

The compounds that met the criteria for in vivo potency were also tested for safety. The capacity of a compound to trigger a pro-inflammatory response was assessed by measuring the expression of the interferon-inducible gene IFIT in the liver. Additionally, the level of ALT following administration of a compound was also measured. Compounds RG6370 and RG3054 increased the expression of IFIT, suggesting a potential pro-inflammatory response.

Based on these HCV replicon assays, the MRP2 assays, and in vivo potency and safety studies, two compounds, RG6650 and RG2634, met the criteria established for selection of a suitably potent and safe compound.

Onset of Action

To determine whether RG6650 and RG2634 could be distinguished by onset of action, groups of mice were treated RG2634, suggesting a more rapid onset of action as measured by ALDOA mRNA de-repression.

Example 4: HCV RNA Level Reduction in Response to miR-122 Inhibition

Due to host-pathogen specificity, HCV can only infect humans and chimpanzees. As such, smaller species, such as mice, that are typically used for experimental in vivo studies cannot be infected with HCV for testing of candidate agents for the treatment of HCV infection. To address this problem, human liver chimeric mouse models may be utilized (see, e.g., Bissig et al., Proc Nat Acad Sci US A, 2007, 104: 20507-20511; Bissig et al., J Clin Invest., 2010, 120: 924-930). In this model, the livers of immunodeficient mice are repopulated with human hepatocytes, resulting in a chimeric liver in which most of the hepatocytes are human hepatocytes. The mice are then infected with HCV and treated with anti-HCV agents. This mouse model is commercially available from, for example, PhoenixBio.

Treatment of HCV-Infected Human Chimeric Liver Mice

Anti-miR-122 compounds were tested in a human chimeric liver mouse model of HCV infection. The livers of immunodeficient mice were repopulated with human hepatocytes, resulting in a chimeric liver in which most of the hepatocytes are human hepatocytes. Six weeks following inoculation with HCV genotype 1a, a baseline viral titer was obtained for each animal included in the study.

Groups of four animals each were treated with PBS, RG-101 at a dose of 45 mg/kg, or RG6650 at a dose of 60 mg/kg. Blood was collected on Days 3, 7, 10, 14, 21, 28, 35, 42, and 49. The study was terminated on day 49.

As shown in FIG. 1, treatment with both RG-101 and RG6650 resulted in significant reductions in viral titer, as measured by serum HCV RNA. RG6650 treatment resulted in a greater than 2-log reduction in serum HCV RNA in HCV-infected animals.

These results demonstrate that, following a single administration of GalNAc-conjugated modified oligonucleotide RG6650, HCV viral titer was significantly reduced in HCV-infected animals, with an early onset and sustained duration of action.

As demonstrated herein, RG6650 is a potent inhibitor of HCV replication, and importantly does not substantially interfere with MRP2 transporter activity in vitro. Accordingly, RG6650 has been identified as a candidate therapeutic agent for the treatment of HCV infection.

Pharmacodynamic Activity of Anti-miR-122 Compounds Following Oral Administration An experiment was performed to determine whether oral administration of RG6650 would results in pharmacodynamic modulation of miR-122 in liver. Also tested was RG7443, the unconjugated anti-miR of RG6650. While an unconjugated anti-miR-122 is not as effective as a GalNAc-conjugated for the inhibition of miR-122 in the treatment of HCV, it was included for comparison in the oral administration study.

Groups of five mice each were treated with RG6650 or RG7443 as shown in Tables 6 and 7, where "s.c." indicates subcutaneous administration and "p.o." indicates oral administration. Anti-miR compounds were delivered in PBS for subcutaneous administration. Orally administered anti-miR compounds were prepared in a solution of PBS and 0.3 M sodium bicarbonate (BC) was added to a pH of 9.5. For oral dosing, animals were fasted for 12 hours prior. For all treatment groups, mice were administered a single dose and sacrificed four days later. Liver tissue was collected for pharmacodynamic and pharmacokinetic analyses. RNA was isolated from liver and kidney. ALDOA depression in the liver was measured.

TABLE 6

PD Effects Following Oral or S.C. Administration of Anti-miR

| Group | Compound Type | Treatment | Dose mg/kg | Route | Liver PD Sig | Std Dev |
|---|---|---|---|---|---|---|
| 1 | | PBS | 0 | s.c. | 0.0000 | 0.1029 |
| 2 | 9-mer + GalNAc | RG6650 in PBS | 30 | s.c. | 1.704 | 0.3447 |
| 3 | 9-mer | RG7443 in PBS | 30 | s.c. | 1.945 | 0.3543 |
| 5 | 9-mer | BC | 0 | p.o. | 0.0000 | 0.0941 |
| 6 | 9-mer + GalNAc | RG6650 in BC | 100 | p.o. | 1.84 | 0.3249 |
| 7 | 9-mer | RG7443 in BC | 100 | p.o. | 0.3448 | 0.2453 |

TABLE 7

Anti-miR Amounts in Liver Tissues Following Oral or S.C. Administration

| Group | Compound Type | Treatment | Dose mg/kg | Route | Liver Mean ug/g | Std Dev |
|---|---|---|---|---|---|---|
| 1 | | PBS | 0 | s.c. | | |
| 2 | 9-mer + GalNAc | RG6650 in PBS | 30 | s.c. | 13.94 | 1.357 |
| 3 | 9-mer | RG7443 in PBS | 30 | s.c. | 1.48 | 0.239 |
| 5 | 9-mer | BC | 0 | p.o. | | |
| 6 | 9-mer + GalNAc | RG6650 in BC | 100 | p.o. | 0.54* | n.d. |
| 7 | 9-mer | RG7443 in BC | 100 | p.o. | <0.4 | |

For RG6650 in liver (*), results in all but one animal were non-quantifiable, thus data from only one animal is reported.

Subcutaneous administration of both unconjugated and GalNAc-conjugated anti-miR-122 compound resulted in derepression of ALDOA in the liver. While oral administration of the unconjugated anti-miR-122 compound RG7443 did not produce a substantial PD effect in the liver, oral administration of the GalNAc-conjugated compound RG6650 yielded a PD effect comparable to that observed following subcutaneous administration. These data demonstrate that the GalNAc-conjugated anti-miR-122 compound RG6650 is an effective inhibitor of miR-122 following both oral and subcutaneous administration.

Free Uptake of Anti-miR-122 Compound in Primary Human Hepatocytes

To further compare the activity of RG-101, RG6650 and RG7443, primary human hepatocytes (PPH) were treated with each compound. As ASGPR expression by PHH is downregulated after plating, 3D PHH spheroids were formed using CCL-163 feeder cells and CellAble plates (Toyo Gosei Co., Japan). Four days following plating on feeder cells, PPH were treated with anti-miR at the following doses: 0.0001 nM, 0.001 nM, 0.01 nM, 0.1 nM, 1 nM, 10 nM, or 100 nM. A control group was treated with PBS. After three days, cells were harvested, RNA was isolated and ALDOA levels were measured by RT-PCR. The EC50 for each compound was calculated. The EC50 for RG-101, RG660 and RG7443 was 6.0 nM, 2.07 nM, and 1.91 pM, respectively. The activity of the GalNAc-conjugated 9-mer was comparable to the activity of RG-101, which has shown effective reduction of HCV titer in the clinic. Further, the GalNAc conjugate dramatically enhanced activity of the 9-mer anti-miR-122 as indicated by a ~1000-fold decrease of EC50 (2.07 nM for RG6650 compared to 1.91 pM for RG7443). Thus, in primary human hepatocytes, the GalNAc-conjugated anti-miR-122 is significantly more active at lower doses than the unconjugated anti-miR-122.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, GENBANK® accession numbers, and the like) cited in the present application is specifically incorporated herein by reference in its entirety.

The invention claimed is:

1. A compound of the structure:

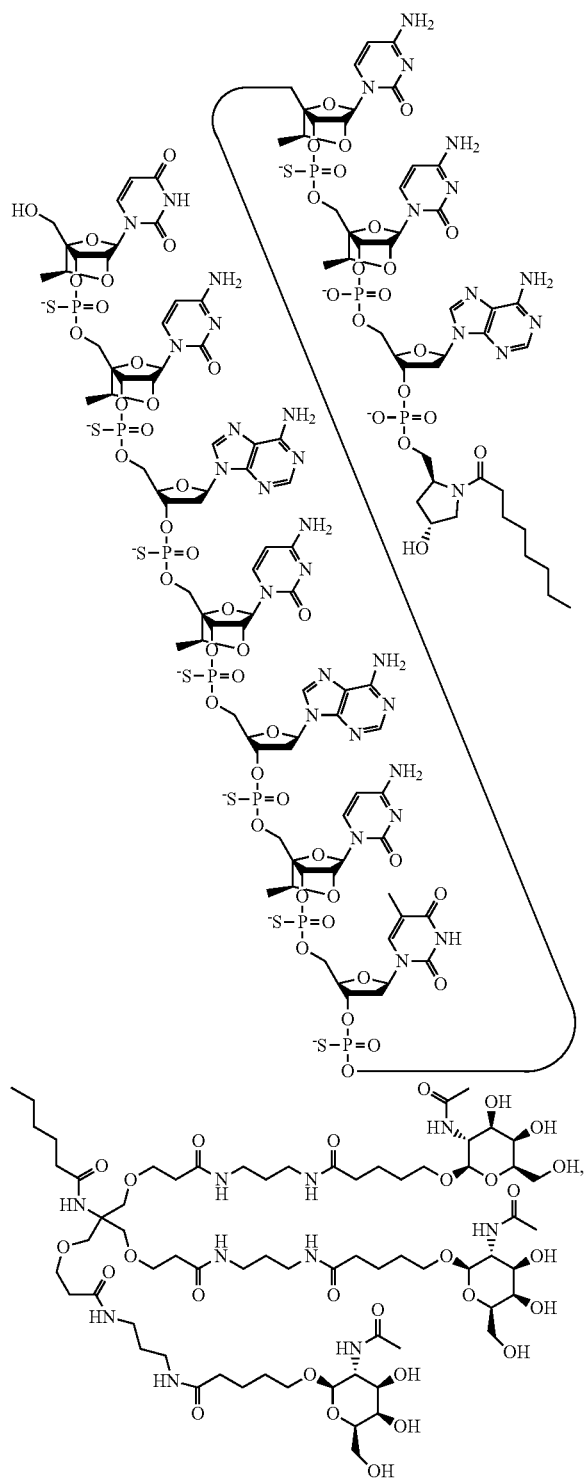

or a pharmaceutically acceptable salt thereof.

2. The compound of claim 1, which is a pharmaceutically acceptable salt of the structure.

3. The compound of claim 2, which is a sodium salt of the structure.

4. A pharmaceutical composition comprising a compound of claim 1 and a pharmaceutically acceptable diluent.

5. The pharmaceutical composition of claim 4, wherein the pharmaceutically acceptable diluent is an aqueous solution.

6. The pharmaceutical composition of claim 5, wherein the aqueous solution is a saline solution.

7. A pharmaceutical composition comprising a compound of claim 1, which is a lyophilized composition.

8. A pharmaceutical composition consisting essentially of a compound of claim 1 in a saline solution.

9. A method of inhibiting the activity of miR-122 in a cell comprising contacting a cell with a compound of claim 1.

10. A method of treating HCV infection comprising administering to an HCV-infected subject at least one dose of a compound of claim 1.

11. A method of treating hepatitis C virus (HCV) infection comprising administering at least one dose of a compound of claim 1 and at least one direct-acting antiviral (DAA) to an HCV-infected subject during a treatment period, wherein the duration of the treatment period is 12 weeks or less, and wherein a start dose of the compound is administered at the start of the treatment period and an end dose of the compound is administered at the end of the treatment period, (ii) a start dose of the compound is administered at the start of the treatment period, and the start dose is the only dose of the compound administered during the treatment period, or (iii) an end dose of the compound is administered at the end of the treatment period, and the end dose is the only dose of the compound administered during the treatment period.

12. The method of claim 11, wherein the duration of the treatment period is 2 to 10 weeks, 4 to 8 weeks, 2 to 6 weeks, or 1 to 4 weeks.

13. The method of claim 10, where in the HCV-infected subject is infected with genotype 1, genotype 2, genotype 3, genotype 4, genotype 5, or genotype 6.

14. The method of claim 13, wherein the HCV-infected subject is infected with genotype 1a or with genotype 1b.

15. The method of claim 10, wherein the HCV-infected subject is determined to be infected with an HCV having one or more resistance-associated polymorphisms.

16. The method of claim 10, wherein the HCV-infected subject is a treatment-naïve subject.

17. The method of claim 10, wherein the HCV-infected subject has an HCV-associated disease, which is cirrhosis, liver fibrosis, steatohepatitis, steatosis, or hepatocellular carcinoma; and/or wherein the HCV-infected subject is an HCV-infected subject with renal impairment; and/or wherein the HCV-infected subject is an HCV/HIV co-infected subject.

18. The method of claim 10, wherein the administering achieves a sustained viral response.

19. The method of claim 11, wherein the DAA is administered daily.

20. The method of claim 11, wherein the DAA is selected from a protease inhibitor, a nucleoside polymerase inhibitor, a nucleotide polymerase inhibitor, a non-nucleoside polymerase inhibitor, an NS3B inhibitor, an NS3/4A inhibitor, an NS4A inhibitor, an NS5A inhibitor, an NS5B inhibitor, and a cyclophilin inhibitor.

21. The method of claim 11, wherein the DAA is selected from one or more of sofosbuvir, ledipasvir, ombitasvir, dasabuvir, glecaprevir, pibrentasvir, elbasvir, grazoprevir, ribavirin, ombitasvir, paritaprevir, ritonavir, boceprevir, vaniprevir, asunaprevir, daclatasvir, simeprevir, mericitabine, tegobuvir, danoprevir, sovaprevir, voxilaprevir, velpatasvir, and GSK2878175.

22. The method of claim 10, wherein the dose of the compound is less than or equal to 4.0 mg/kg, less than or equal to 3.5 mg/kg, less than or equal to 3.0 mg/kg, less than or equal to 2.5 mg/kg, less than or equal to 2.0 mg/kg, less than or equal to 1.5 mg/kg, less than or equal to 1.0 mg/kg, or less than or equal to 0.5 mg/kg.

* * * * *

SEQUENCE LISTING

```
<160> NUMBER OF SEQ ID NOS: 2

<210> SEQ ID NO 1
<211> LENGTH: 22
<212> TYPE: RNA
<213> ORGANISM: Homo sapiens

<400> SEQUENCE: 1
uggaguguga caauguguguu ug                                          22

<210> SEQ ID NO 2
<211> LENGTH: 18
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: RNA

<400> SEQUENCE: 2
acaccattgu cacactcc                                                18
```